United States Patent [19]

Oh et al.

[11] Patent Number: 5,168,057
[45] Date of Patent: Dec. 1, 1992

[54] TRIFUNCTIONAL CONJUGATES

[75] Inventors: Chan S. Oh, Diamond Bar; James C. Sternberg, Fullerton, both of Calif.

[73] Assignee: Beckman Instruments, Inc., Fullerton, Calif.

[21] Appl. No.: 768,118

[22] Filed: Sep. 30, 1991

Related U.S. Application Data

[63] Continuation of Ser. No. 103,093, Sep. 30, 1987, abandoned.

[51] Int. Cl.$^5$ ............... C12N 11/00; C12N 11/06; G01N 33/547; G01N 33/532
[52] U.S. Cl. ............ 435/174; 435/7.9; 435/7.92; 435/7.93; 435/177; 435/181; 435/964; 436/518; 436/528; 436/532; 436/537; 436/544; 436/545; 436/819; 530/810; 530/812; 530/816
[58] Field of Search ............ 435/7, 7.1, 7.9, 7.92, 435/7.93, 174, 177, 181; 436/518, 528, 532, 537, 543, 544, 565; 530/810, 812, 816

[56] References Cited

U.S. PATENT DOCUMENTS

| | | | |
|---|---|---|---|
| 3,935,074 | 1/1976 | Rubenstein et al. | 195/103 |
| 4,067,774 | 1/1978 | Rubenstein et al. | 435/7 |
| 4,130,462 | 12/1978 | Rubenstein et al. | 195/103 |
| 4,134,792 | 1/1979 | Boguslaski et al. | 195/99 |
| 4,228,237 | 10/1980 | Hevey et al. | 435/7 |
| 4,233,402 | 11/1980 | Maggio et al. | 435/7 |
| 4,238,565 | 12/1980 | Horaby et al. | 435/7 |
| 4,298,685 | 11/1981 | Farikh et al. | 435/7 |
| 4,506,009 | 3/1985 | Lenhoff et al. | 435/7 |
| 4,550,075 | 10/1985 | Bacquet et al. | 435/7 |
| 4,604,365 | 8/1986 | O'Neill et al. | 436/528 |
| 4,608,339 | 8/1986 | Benovic et al. | 435/7 |
| 4,629,690 | 12/1986 | Weng et al. | 435/7 |
| 4,663,278 | 5/1987 | DiNello | 435/7 |
| 4,687,732 | 8/1987 | Ward et al. | 436/545 X |
| 4,687,735 | 8/1987 | DiNello et al. | 435/7 |
| 4,722,906 | 2/1988 | Guire | 530/389 X |

FOREIGN PATENT DOCUMENTS

| | | |
|---|---|---|
| 055869 | 7/1982 | European Pat. Off. . |
| 20070685 | 1/1983 | European Pat. Off. . |
| 0183901 | 6/1986 | European Pat. Off. . |
| 2029011 | 3/1980 | United Kingdom . |

OTHER PUBLICATIONS

Flygare et al., "Affinity Precipitation of Enzymes", *Appl. Biochem. and Biotech.*, 7, 59-61 (1982).

Flygare et al., "Affinity Precipitation of Dehydrogenases", *Anal. Biochem.* 133, 409-416 (1983).

Gibbons et al., "Homogeneous Enzyme Immunoassay for Proteins Employing B-Galactosidase", *Anal. Biochem.*, 102, 167-170 (1980).

Green et al., "The Use of Bifunctional Biotinyl Compounds to Determine the Arrangement of Subunits in Avidin", *Biochemistry*, 125, 781-791 (1971).

Guire et al., "Photochemical Coupling of Enzymes to Mammalian Cells" *Pharm. Res. Com.*, 9 (2), 131-141 (1977).

Kohno et al., "A Novel Enzyme Immunoassay of Anti--Insulin IgC in Guinea Pig Serum", *Biochem. Biophys. Res. Comm.*, 147(2), 644-649 (1987).

Larsson et al., "Affinity Precipitation of Enzymes", *Elsevier/North-Holland Biomedical Press*, 98(2), 330-333 (1979).

(List continued on next page.)

*Primary Examiner*—David M. Naff
*Attorney, Agent, or Firm*—William H. May; Arnold Grant; Richard P. Burgoon, Jr.

[57] ABSTRACT

A trifunctional conjugate is provided having three chemical moieties, attached through a spacer moiety. At least two of the chemical moieties are relatively small molecules, usually less than about 7,000 Daltons in size. The spacer moiety is selected to impart certain steric properties to the conjugate. In one embodiment, the binding of a macromolecular specific binding partner to one of the chemical mouths sterically inhibits the binding of a different macromolecule to another chemical moiety. In another embodiment, the binding of a first chemical moiety to a macromolecule restricts the subsequent binding of a second chemical moiety to a proximate location on the same macromolecule.

30 Claims, 12 Drawing Sheets

OTHER PUBLICATIONS

Lee et al., "Synthesis of the Bifunctional Dinucleotide AMP-ATP and its Application in General Ligand Affinity Chromatography", *J. Solid Phase Biochem.*, 2(1), 31-39 (1977).

Litman et al., "Enzyme Channeling Immunoassay: A New Homogeneous Enzyme Immunoassay Technique", *Anal. Biochem.*, 106, 223-229 (1980).

Morris et al., "Flavin Adenine Dinucleotide as a Label in Homogeneous Colorimetric Immunoassays", *Anal. Chem.* 53(4), 658-665 (1981).

Ngo et al., "Enzyme Modulators as Tools for the Development of HomoGeneous Enzyme Immunoassays", *Elsevier/North-Holland Biomedical Press*, 116(2), 285-288 (1980).

Oellerich, "Enzyme Immunoassay: A Review", *J. Clin. Chem. Biochem.*, 22, 895-904 (1984).

Patel et al., "Chemiluminescence Energy Transfer: A New Technique Applicable to the Study of Ligand-Ligand Interactions in Living Systems", *Anal. Biochem.*, 129, 162-169 (1983).

Simpson et al., "Chemiluminèscent Labels in Immunoassay", in: Deluca et al., *Bioluminescence and Chemiluminescence*, 673-679 (cademic Press, 1981).

Smith et al., "The Utility of Photo-Affinity Labels as 'Mapping' Reagents", *Biochem. J.* 141, 51-56 (1974).

Sternberg, "A Rate Nephelometer for Measuring Specific Proteins by Immunoprecipitin Reactions", *Clin. Chem.* 23(8), 1456-1464 (1977).

Stryer, "Fluorescence Energy Transfer as a Spectroscopic Ruler", *Ann. Rev. Biochem.*, 47, 819-846 (1978).

Ullman et al., "Fluorescent Excitation Transfer Immunoassay", *J. Biol. Chem.*, 251(14), 4172-4178 (1976).

Weeks et al., "Acridinium Esters as High-Specific Activity Labels in Immunoassay", *Clin. Chem.*, 29(8), 1474-1479 (1983).

Whitehead et al., "Analytical Luminescence: Its Potential in the Clinical Laboratory", Clin. Chem., 25(9), 1531-1545 (1979).

Product publication: Microgenics' CEDIA Digoxin Assay Product Insert (Microgenics Corp., Concord, CA), Mar., 1987.

Tang, S. C., et al., "Chromium (III) azidoaquo complexes . . .", *Chem. Abs., Section 78-Inorganic Chem.*, 77:147107p (1972).

Bush, M. E., et al., "Antigen Recognition and the Immune Response: . . .", *J. Exp. Med.* 136:1478-1483 (1972).

Alkan, S. S., et al., "Antigen Recognition and the Immune Response: . . .", *J. Exp. Med.* 135:1228-1246 (1972).

Woods, V., et al., "The Capacity of Bifunctional Antigens . . .", *Immunochemistry* 12:379-382 (1975).

Green M. M., et al., "The Use of Bifunctional Biotinyl Compounds . . .", *Biochem J.* 125:781-791 (1971).

Green, N. M., et al., "Electronic Microscopy of Complexes . . .", *J. Mol. Biol.* 56:203:206 (1971).

Stevenson, R. L. and Freiser, H. "Tridentate Ligands derived from substitution . . .", *Chem. Abs.* 67:9736, Abstract 103293K (1967).

Microbiology, 3d. Ed., "Immunology" pp. 292-295, 298-317, 324-355. Davis, B. D., et al., Eds. Harper & Row (1980).

TRIFUNCTIONAL CONJUGATES

This is a continuation of copending application Ser. No. 07/103,093 filed on Sep. 30, 1987, now abandoned.

BACKGROUND OF THE INVENTION

Reference is made to copending application Ser. No. 07/103,237, filed Sep. 30, 1987, now abandoned, entitled "Novel Bidentate Conjugate and Method of Use Thereof", which is filed concurrently herewith in the names of Paul Harris and Chan S. Oh.

1. Specific Binding Assays

Methods for measuring immunochemical or other types of specific binding reactions have become widely accepted in the field of medical testing in recent years. Generally speaking, an immunochemical reaction involves the reaction between at least one antigen and at least one antibody. An antigen is ordinarily a substance, such as a protein or carbohydrate, which is capable of inducing an immune response; i.e., antibody production, when introduced into an animal or human body. The antibodies produced as a result of the immune response are bivalent in nature, generally being depicted as a "Y", wherein each arm of the "Y" is capable of binding to the antigen which induced production of the antibody. The presence of a particular antigen or antibody in a patient's test sample may indicate a disease state or a bodily condition, such as pregnancy. An immunochemical reaction is one type of specific binding reaction.

Antibody fragments are often used in addition to or in place of whole antibodies in an immunoassay. Generally, there are three different types of antibody fragments. The first type of fragment is designated as either Fab, or F(ab), and is a single arm of the antibody which has been directly cleaved from the whole antibody, usually through digestion by the enzyme papain. Each Fab fragment is monovalent, and has a molecular weight of about 50,000 Daltons, compared to the approximate 150,000 Dalton size of the whole antibody. The second type of fragment is designated as F(ab')$_2$, and consists of both antibody arms, still linked together, but minus the tail which is removed by pepsin digestion. The divalent F(ab')$_2$ fragment has a molecular weight of about 100,000 Daltons, and can be further cleaved into two separate monovalent Fab' fragments (the third type of antibody fragment), also designated as F(ab'), each having a molecular weight of about 50,000 Daltons.

The site on the antigen to which an arm of the antibody binds is referred to as an epitope. Most antigens are polyepitopic, having multiple, and often repeating, binding sites for antibodies. It is the polyepitopic nature of antigens and the bivalent character of antibodies, including F(ab')$_2$ fragments, which enable large antibody:antigen complexes of varying sizes, otherwise known as immunocomplexes, to be formed in an immunoassay.

One particular type of immunoassay which takes advantage of this feature is the sandwich immunoassay, wherein a ternary immunocomplex is formed. The most common type of sandwich immunoassay employs a first insolubilized antibody, usually bound to a solid support, and a second labeled antibody. Each antibody is specific for the antigen of interest (i.e., the analyte to be measured) and binds to a different epitope on the antigen. Preferably, the first antibody binds to an epitope which is remote from the epitope to which the second antibody binds. A ternary complex of insoluble antibody:antigen:labeled antibody is formed where the antigen of interest is contacted with the first and second antibodies. Because each antibody is required to bind to only one antigen, all three types of antibody fragments may be used in this type of method. The presence or absence of the antigen of interest is indicated by the presence or absence of the labeled antibody on the solid support. Ordinarily, the insolubilized phase of the reaction must be separated from the liquid phase in order for either the bound or free labeled antibody to be quantified. Such a reaction is referred to as a heterogenous type of reaction, due to the required separation step.

Nephelometry and turbidimetry require the formation of large aggregates of, e.g., antibody and antigen. Because each antibody must bind to two different antigen molecules, the monovalent Fab and Fab' fragments are generally ineffective in these methods. The large aggregates cause a change in the light scatter of the solution, and are capable of measurement by nephelometric or turbidimetric methods. These methods do not require the use of traditional labels, such as enzymes, radioactive isotopes, fluorescent, or chemiluminescent compounds, to detect the amount of complex formed. Rather, nephelometric and turbidimetric methods directly measure the amount of complex formed. Because no separation step is required, nephelometry and turbidimetry are referred to as homogenous immunoassays.

The multiepitopic nature of the antigen and bivalent character of the antibody will, depending on the amount of antigen and/or antibody present, allow the formation of antigen:antibody complexes large enough to scatter light. Ordinarily, an excess of antibody is used in conjunction with a finite amount of antigen obtained from, e.g., a patient's blood, serum, cerebrospinal fluid (CSF), or urine sample. In such a case, the amount of antigen present in the sample will be the limiting factor in determining the amount and size of antigen:antibody aggregates formed.

In turbidimetry, the reduction of light transmitted through the suspension of particles, or aggregates, is measured. The reduction is caused by reflection, scatter, and absorption of the light by the aggregates. In nephelometry, it is the light scattered or reflected toward a detector that is not in the direct path of light which is measured. In both turbidimetry or nephelometry, the rate of change in light scatter may also be measured as an indication of the amount of antigen present.

Nephelometric procedures have become a convenient method for monitoring antigen:antibody reactions at an early stage, by detecting the rate of growth of complexes capable of scattering light before the complexes separate out of solution as immunoprecipitates. The growth of these complexes begins as a buildup of aggregates which ultimately become large enough to function as "scattering centers". Sternberg, J. C., A Rate Nephelometer for Measuring Specific Proteins by Immunoprecipitation Reactions, *Clin. Chem.*, 23:8, 1456-1464 (1977). The formation of scattering centers can be accelerated by the use of hydrophilic nonionic polymers, such as dextran or polyethylene glycol, which increase the probability of protein-protein interaction by excluding a significant fraction of water. The use of polymers in an immunonephelometric assay also gives the advantages of increased sensitivity and less antiserum consumption.

2. Nephelometric Inhibition Immunoassays for Haptens

Haptens pose a unique problem in immunoassay methods. Haptens are relatively small monovalent molecules, sometimes regarded as incomplete or fragmentary antigens. One common class of haptens is drugs. Theophylline, for example, is a member of this particular subclass of haptens. A hapten is, in and of itself, incapable of inducing an immune response in a human or animal body. This is because haptens are generally too small to be recognized by the body's immune system. However, when coupled to a carrier, such as a protein, the hapten:carrier protein conjugate acts as an antigen which is large enough to induce antibody production. In this way, antibodies can be raised against a hapten. Unlike the relatively large antigens, however, the small hapten molecule is not itself multiepitopic. For this reason, haptens are incapable of forming large complexes or agglomerates with the antibody which has been produced against the hapten.

Consequently, in order to perform nephelometric or turbidimetric assays for haptens, such as in therapeutic drug monitoring, a technique known as nephelometric inhibition immunoassay (NIIA) has been developed, wherein the hapten acts as an inhibitor to complex formation. In traditional NIIA, a second conjugate known as a "developer antigen" is used to develop complexes of sufficient size to cause detectable light scattering. The developer antigen is formed from a second carrier, also usually a protein, conjugated to a multiplicity of hapten molecules. In this way the developer antigen acts as a "polyvalent hapten" which is capable of aggregating with more than one antibody molecule to ultimately form scattering centers. The second carrier protein is sometimes referred to as the "label". The monovalent free hapten present in a patient's test sample acts to inhibit the amount of developer antigen:antibody complexing, by binding to one or both arms of the antibody molecule, thereby reducing complex formation and diminishing the amount of light scatter. Because of the nature of the inhibition immunoassay, both the amount and the rate of the increase detected in light scatter are inversely proportional to the amount of hapten present in the patient's sample.

Several problems have been encountered with prior art turbidimetric or nephelometric inhibition immunoassays. One problem concerns the developer antigen reagent. The traditional developer antigen is generally unstable and requires special storage conditions. The requirement for special storage conditions arises from the fact that the carrier protein of the developer antigen, being a natural proteinaceous substance, degrades relatively rapidly during manufacture as well as during storage. At room temperature, a typical developer antigen can be expected to last only about eight hours. Even at refrigeration temperatures, most developer antigens exhibit a shelf life of only about six months. This greatly compounds the problems of manufacture and distribution and adds to the cost of such products. Moreover, because the carrier protein for the developer antigen is derived from natural sources, considerable variation is encountered in the properties of these proteins. The traditional developer antigen reagent must be carefully prepared, purified, and characterized to insure uniform reactivity. This characterization process is the most expensive aspect of the manufacture of prior art developer antigens.

Prior art NIIA's have also been found to possess limited sensitivity in relation to other types of immunoassays, such as the sandwich immunoassay. This sensitivity limitation results primarily from the scatter caused by other components of the serum sample. For this reason, a test sample must be diluted significantly before being added to the reaction medium of an NIIA, thereby also diluting the concentration of analyte in the reaction medium. In other types of immunoassays, such as the sandwich immunoassay, about 100–200 $\mu$L of sample are typically added to the reaction medium. In contrast, only about 1–3 $\mu$L of sample are ordinarily injected into the reaction medium for an NIIA. One method that has been suggested for improving sensitivity involves optimizing the hapten:carrier ratio of the developer antigen, as disclosed in U.S. Pat. No. 4,604,365. High and low hapten:carrier ratios have been reported to result in moderate sensitivity, with improved sensitivity being observed at intermediate ratios. This method, however, is time consuming and fails to show marked increases in NIIA sensitivity.

Yet another problem encountered with the prior art NIIA's involves a phenomenon known as "nonproductive binding". Nonproductive binding occurs, for example, where the two binding arms of the same antibody bind to two hapten moieties on the same developer antigen. In such an instance, there can be no cross-linking with other developer antigens, because there is no free arm on the antibody to bind with another developer antigen. This results in the inefficient use of expensive antibody and developer antigen reagents.

Due to the ease and convenience of the homogenous turbidimetric and nephelometric inhibition immunoassays for haptens, it would be advantageous to have a stable developer antigen which can readily be manufactured to possess consistent characteristics and which exhibits a long shelf life at room temperatures. It would also be advantageous to improve the sensitivity of the NIIA and to reduce the occurrence of nonproductive binding.

3. Prior Art Bifunctional Conjugates

There are several small molecule bifunctional conjugates which exist in the prior art. What is meant by the term "small molecule bifunctional conjugate" is a conjugate which employs two small molecules which are linked together through a spacer moiety. The spacer moiety may be so small as to comprise only one chemical bond (i.e., zero atoms in the spacer). Generally, these molecules are on the order of about 7,000 Daltons or smaller in size. Both molecules act as small molecule ligands and, as such, are each capable of interacting with a substance having a specific binding affinity for the small molecule; i.e., its specific binding partner. This definition specifically excludes conjugates which employ one or more large molecules and/or conjugates which employ one or more chemical moieties which do not have a specific binding partner. For example, the typical enzyme labeled antibody in a sandwich immunoassay is excluded for both reasons; i.e., the antibody moiety is a large macromolecule, generally greater than about 150,000 Daltons in size, and the enzyme moiety, although it acts on a substrate, is not generally considered to be the specific binding partner for the substrate. Also excluded are heterobifunctional cross-linking agents which utilize two chemically reactive groups, rather than two small molecule ligands, one at each end of the conjugate.

There are two classes of small molecule bifunctional conjugates existing in the prior art. The first class of conjugates, known as the homobifunctional conjugate employs identical chemical moieties at each end of the conjugate. The homobifunctional conjugates are generally designed to bring together, or unite, the identical specific binding partner with which each chemical moiety interacts. Where the specific binding partner is polyvalent, large aggregates may be formed.

For example, a Bis-NAD homobifunctional conjugate has been proposed as a precipitating agent for enzymes. Larsson, P. and Mosbach, K., Affinity Precipitation of Enzymes, FEBS Letters, 98(2), 333-330 (1979). The Bis-NAD conjugate, comprising two NAD moieties separated by a 17 Å spacer moiety, is capable of precipitating the enzyme lactate dehydrogenase (LDH) out of solution by specifically binding to a large LDH molecule at each end of the Bis-NAD. Because each large LDH molecule has multiple binding sites for NAD, large aggregates, similar to those formed in nephelometry, can be obtained. These large aggregates precipitate out of solution carrying along the enzyme. Similar uses of Bis-nucleotides of varying spacer lengths have also been proposed.

Another example of a homobifunctional conjugate which has found application in the prior art is the Bis-biotin conjugate used to examine the structure of avidin. Green, N. M., Konieczny, L., Toms, E. J., and Valentine, R. C., The Use of Bifunctional Biotinyl Compounds to Determine the Arrangement of Subunits in Avidin, *Biochemistry*, 125, 781-791 (1971). Where the two biotin moieties of the Bis-biotin conjugate were joined by a spacer moiety of approximately 18 Å, strong complexes or polymers were formed with the multivalent macromolecule avidin.

The second class of prior art small molecule bifunctional conjugates is the heterobifunctional conjugate. In contrast to the homobifunctional conjugate, the heterobifunctional conjugate employs a different chemical moiety at each end of the conjugate. Each of these chemical moieties is capable of interacting with a different specific binding partner. These prior art heterobifunctional conjugates have been used almost exclusively as modulators, wherein the binding of a specific binding partner to one of the chemical moieties hinders or precludes the simultaneous binding of the corresponding specific binding partner to the other chemical moiety. Simultaneous binding at both ends of the heterobifunctional conjugate is precluded by steric hindrance, generally caused by the use of shorter spacer lengths than those required to achieve the desired simultaneous binding where homobifunctional conjugates are employed as described above. In other words, the binding of a macromolecular specific binding partner to the modulator moiety of the conjugate sterically inhibits the binding of the specific binding partner to the chemical moiety responsible for producing signal.

The prior art heterobifunctional conjugates generally employ a small molecule ligand of interest, usually an analyte, as one of the chemical moieties of the conjugate. This chemical moiety can compete with free analyte, such as from a test sample, for a limited amount of specific binding partner for the analyte. The other chemical moiety of the heterobifunctional conjugate is usually a "surrogate" label such as an enzyme modulator or a prosthetic group or other cofactor for an enzyme. The surrogate label modulates the activity of the indicator label, usually an enzyme. These types of prior art heterobifunctional conjugates are generally of use in homogenous enzyme immunoassays, because the degree of activity of the enzyme is directly influenced by the antigen:antibody reaction. No separation step is required to determine the amount of enzyme activity attributable to the bound enzyme versus the activity attributable to the free enzyme, as in heterogenous enzyme immunoassays.

The enzyme modulated immunoassay is based on the ability of the small molecule ligand:enzyme modulator heterobifunctional conjugate to influence the activity of the indicator enzyme. See, for example, U.S. Pat. No. 4,134,792, which also discloses larger surrogate labeled conjugates. In this instance, the spacer moiety between the ligand moiety and the enzyme modulator moiety is relatively short, preferably being on the order of about 1-10 carbon atoms or heteroatoms in length; i.e., about 1 3 to about 14.0 Å.

The small molecule ligand:enzyme modulator heterobifunctional conjugate competes with ligand from a test sample for a limited amount of antibody. If the small molecule ligand:enzyme modulator heterobifunctional conjugate is bound to the antibody; i.e., through the ligand moiety of the conjugate, the enzyme modulator cannot affect the activity of the indicator enzyme. Modulators which increase or decrease the enzyme activity of the indicator enzyme can be used, although modulators which decrease enzyme activity; i.e., enzyme inhibitors, are more commonly used. In assays employing an inhibiting modulator, the observed enzyme activity will be inversely proportional to the concentration of analyte.

A similar type of homogenous enzyme immunoassay is based on the use of a small molecule ligand:enzyme cofactor heterobifunctional conjugate. In a broad sense, an enzyme cofactor operates as a positive enzyme modulator; i.e., a modulator which increases enzyme activity. Generally, enzymes may be divided into two groups: (1) enzymes where enzymatic activity is due solely to the protein nature of the enzyme; and, (2) enzymes where optimal enzymatic activity is dependent on a heat-stable, non-protein structure called a cofactor. Immunoassays employing enzymes of this second group lend themselves to modulation through the use of a small molecule ligand: enzyme cofactor heterobifunctional conjugate.

Cofactors vary in nature from simple inorganic ions to more complex organic materials, many of which are derivatives of vitamins, such as biotin and flavin adenine dinucleotide (FAD). The organic cofactors are often referred to as coenzymes. In certain cases, as is typical with prosthetic groups, the cofactor is firmly bound, usually through a covalent linkage, to the protein moiety of the parent enzyme which is otherwise individually known as the apoenzyme. In the classical jargon of enzymology, the complete, enzymatically active enzyme:cofactor complex is termed a holoenzyme.

Residues of certain cofactors such as FAD, flavin mononucleotide (FMN), or heme, for example, provide particularly good enzyme prosthetic groups for use in a small molecule ligand:enzyme prosthetic group heterobifunctional conjugate. See, for example, U.S. Pat. No. 4,238,565, which also discloses larger surrogate labeled conjugates. In this case, the spacer moiety between the ligand moiety and the enzyme prosthetic group moiety is no more than 14 carbon atoms, and more commonly 1-6 carbon atoms or 0-5 heteroatoms in length; i.e., about 1.3 to about 14.0 Å.

According to U.S. Pat. No. 4,238,565, the ligand:prosthetic group heterobifunctional conjugate (for example ligand:FAD) competes with the ligand in a test sample for a limited amount of antibody. If the ligand:

FAD conjugate is bound by the antibody, it can no longer combine with the apoenzyme to form an enzymatically active holoenzyme. The observed enzyme activity is directly related to the concentration of analyte present in the test sample.

The one exception to this modulator type of use of the heterobifunctional conjugate is in the area of column chromatographic purification. A substance may be purified by passing a solution containing the substance through a chromatographic column in one of two ways. In one manner of purification, the column contains attached groups that specifically bind to or otherwise pull specific impurities from the solution. In an alternate manner of purification, groups which specifically bind to the substance sought to be purified are immobilized on the column. These groups pull the desired substance out of solution. In the latter case, the substance must later be eluted from the column.

General ligand affinity chromatography follows the latter approach and is based on the principle that a single immobilized ligand is able to adsorb a family of enzymes, such as dehydrogenases or kinases, with the isolated enzyme being subsequently eluted under conditions favoring biospecific elution. Often a cofactor or cofactor fragment is used as the general ligand.

The insolubilized small molecule heterobifunctional conjugate AMP-ATP has been proposed for use in general ligand affinity chromatography. Lee, C.-Y., Larsson, P. O., and Mosbach, K., Synthesis of the Bifunctional Dinucleotide AMP-ATP and its Application in General Ligand Affinity Chromatography, *J. Solid Phase Biochem.*, 2(1), 31–39 (1977). The ATP moiety (specific for kinases) is attached to a Sepharose® 4B (cross-linked agarose gel, Pharmacia, Uppsala, Sweden) column through a previously bound AMP moiety (specific for dehydrogenases). It has been reported that the ATP and AMP moieties retain their affinity behavior toward kinases and dehydrogenases, respectively, even when both are bound to the Sepharose® column through the AMP moiety. An attempt to prepare a soluble AMP-ATP dinucleotide has proved unsuccessful. Id.

None of these prior art bifunctional conjugates has been applied to nephelometric or turbidimetric assay procedures. Moreover, these prior art bifunctional conjugates lack the versatility and sensitivity that could be achieved with, e.g., a trifunctional conjugate. For example, the small molecule homobifunctional conjugate is useful only for linking up like molecules, while the small molecule heterobifunctional conjugate is limited in application to only certain types of assays which lend themselves to modulation by such a conjugate. It would be advantageous to have a trifunctional conjugate capable of agglomerating dissimilar macromolecules as well as serving a modulating function in a greater variety of immunoassays.

4. The Use of Avidin and Biotin in Immunoassays

Avidin and biotin are both naturally occurring compounds. Avidin is a relatively large macromolecular protein and is found in egg whites. Avidin contains four subunits. Biotin is a relatively small, stable, water-soluble vitamin. Each of the four subunits of an avidin molecule is capable of specifically binding to a molecule of biotin. The binding reaction between avidin and biotin is very strong, with the binding constant being approximately $10^{15}$ L/mole. The very strong nature of this bond has been found to persist even when biotin is conjugated, by means of its carboxyl group, to another molecule, or when avidin is attached to another molecule. When biotin is conjugated to another molecule, the resulting conjugate is usually referred to as a biotinylated compound; e.g., a biotinylated protein. A biotinylated protein may, for example, quickly become strongly bound to a corresponding avidin-attached molecule. This feature of linking up biotinylated compounds with avidin conjugates has been employed, with varying degrees of success, mostly in heterogenous immunoassays.

Two such applications pertain to sandwich immunoassays. In one instance, the avidin:biotin bond is utilized at the label end of the sandwich. This is seen in U.S. Pat. No. 4,228,237, wherein a biotinylated specific binding partner for the ligand to be measured is employed in conjunction with enzyme-labeled avidin. In another instance, the biotin:avidin bond may be used at the insolubilized end of the sandwich formed in a sandwich immunoassay. For example, U.S. Pat. No. 4,298,685 teaches the use of insolubilized avidin which is ordinarily added after the labeled sandwich has been formed in solution. Where the unlabeled antibody of the sandwich has previously been tagged with biotin, the insolubilized avidin is able to capture the labeled sandwich from the solution. These applications are not applicable to nephelometry or turbidimetry. Moreover, the additional conjugation steps required for preparing reagents makes such methods less attractive economically.

Avidin has also been used in homogenous immunoassays as the enzyme modulator label component of a larger surrogate labeled conjugate, which is used in a manner similar to the previously discussed small molecule ligand:enzyme modulator heterobifunctional conjugates. Avidin is the natural inhibitor of biotin-containing enzymes such as pyruvate carboxylase. When the biotin moiety of these enzymes is tied up, i.e., complexed with avidin, the activity of the enzyme ceases or is diminished. This is because biotin is a required cofactor of these enzymes, and, where the biotin moiety is incapable of functioning as a cofactor, enzyme activity is inhibited. Avidin may thus be used as a modulator label, due to its ability to modulate or control the activity of biotin-containing enzymes which, when allowed to act upon a substrate, yield a measurable signal in certain homogenous immunoassay systems.

U.S. Pat. No. 4,550,075 discloses avidin as the modulator label component of a larger labeled conjugate for use in a homogenous immunoassay. The labeled conjugate of U.S. Pat. No. 4,550,075 takes advantage of the large molecular size of avidin, which, at approximately 63,000 Daltons, is considerably larger than most modulator labels; i.e., enzyme inhibitors. This enables avidin to alleviate a steric hindrance problem typically encountered with larger surrogate labeled conjugates. For example, where a small molecule ligand: enzyme modulator heterobifunctional conjugate is used, the relatively small size of the typical low molecular weight enzyme modulator is comparable to that of the ligand portion of the conjugate, and the modulator is therefore able to function effectively in the assay. Where, however, the ligand is much larger than the usual enzyme modulator, such as where the ligand is an antigen, the typical enzyme modulator is dwarfed by the size of the ligand, and the activity of the modulator label is sterically inhibited even in the absence of binding by the ligand component to its specific binding partner.

This steric hindrance problem has been addressed to some extent in the previously cited U.S. Pat. No.

4,238,565, wherein it is suggested that a slightly longer spacer moiety be employed where the ligand is a larger molecule of relatively high molecular weight. In any event, the spacer moiety may not exceed about 14 carbon atoms and 0-5 heteroatoms in length. The objective is that steric hindrance should occur only when the ligand moiety of the conjugate is bound to its specific binding partner, but not while the ligand moiety of the conjugate is free. U.S. Pat. No. 4,550,075, on the other hand, simply takes advantage of the inability of large ligands, such as antigens, to sterically hinder the activity of the macromolecular enzyme modulator avidin. Steric hindrance occurs only when the ligand moiety is bound to its specific binding partner.

The avidin:biotin bond has not been made of use in nephelometric or turbidimetric procedures, although the high specificity and strong nature of the bond would seemingly make it desirable in such procedures. The only use of avidin:biotin in complex formation is the previously noted use of Bis-biotin to agglomerate avidin. Likewise, avidin has not been used to create a desired steric hindrance, but, instead, to avoid steric hindrance where the analyte member of a bifunctional conjugate for use in a modulated assay is a macromolecular antigen. It would be desirable to take advantage of the steric hindrance-inducing ability of the macromolecular specific binding partner avidin, particularly in the area of NIIA's and modulated assays.

5. Prior Art Proximity Assays

There exist in the prior art several types of immunoassays wherein a measurable interaction occurs between the labeled portion of a labeled antigen and the labeled portion of a labeled antibody when the two labels are brought into close proximity with each other; i.e., pursuant to a specific binding reaction between the antigen and the antibody. These immunoassays may be referred to as "proximity assays" because they require that the labels be proximate to each other before a measurable reaction can occur. Where the proximity is caused by the binding of a labeled antigen or hapten, such as an analyte of interest, to a labeled antibody, the signal obtained from the interaction between the proximately located labels can be correlated to the amount of antigen or hapten present in a test sample. Most assays employing proximity labels are competitive assays wherein the amount of signal generated bears an inverse relationship to the amount of analyte present in a sample.

One type of proximity assay, known as an "enzyme channeling" assay, employs as labels an enzyme pair from a multienzyme complex. Multienzyme complexes occur frequently in nature and consist of two or more enzymes that are involved in a sequence of reactions. In other words, the product of one enzyme serves as a substrate for a second enzyme. The product of the second enzyme may serve as the substrate for a third enzyme, and so forth. The enzyme channeling assay utilizes two enzymes which operate in sequence in a multienzyme complex. For convenience, the two enzymes are referred to as a first enzyme and a second enzyme, with the product of the first enzyme serving as a substrate for the second enzyme.

One example of an enzyme channeling assay utilizes hexokinase (HK) and glucose-6-phosphate dehydrogenase (G6PDH) as the first and second enzymes, respectively. Litman, D. J., Hanlon, T. M., and Ullman, E. F., Enzyme Channeling Immunoassay: A new Homogenous Enzyme Immunoassay Technique, *Anal. Biochem.*, 106, 223-229 (1980). The first enzyme (HK) is attached to a finite amount of antibody to the antigen of interest. Both the second enzyme (G6PDH) and antigen identical or analogous to the analyte of interest are bound to microporous beads. In the absence of free antigen, contributed by a patient's test sample, a "channeled system" will exist wherein all of the antibody-bound first enzyme will be bound to the bead through the previously bound antigen. In an "unchanneled system" all of the first enzyme will remain free. This occurs where sufficient free antigen, contributed by test sample, competes so effectively with the bound antigen for a limited amount of enzyme-labeled antibody that none of the enzyme-labeled antibody can bind to the bead.

The amount of enzyme-labeled antibody bound to the bead is a direct function of the amount of free antigen present in a test sample, and can be correlated to the degree of channeling obtained in a particular system. The degree of channeling, or "channeling efficiency", is ordinarily detected by measuring the amount of product generated by the second enzyme. This product is generated only where the second enzyme is able to act on the product generated by the first enzyme in close proximity to the second enzyme.

For example, where HK is the first enzyme, its reaction product, glucose-6-phosphate, will be acted upon by the bound second enzyme, G6PDH, where the HK-labeled antibody is also bound to the bead. In this instance, the glucose-6-phosphate is generated within the vicinity of a high local concentration of G6PDH, such that the G6PDH is able to act on the glucose-6-phosphate before it escapes into the bulk solution. The "channeling efficiency" of the system is the amount of first enzyme product converted by the second enzyme before the product escapes into bulk solution and is an inverse measure of the amount of analyte present in a test sample.

Another type of proximity assay utilizes a phenomenon known as energy transfer. In an energy transfer proximity assay, the measured interaction is usually a change or shift in light emission, which is caused by the transfer of light, or energy, from one label to a second proximately located label. The label from which the energy is transferred is referred to as the "donor label", while the label to which the energy is transferred is referred to as the "acceptor label".

One particular energy transfer assay employs chemiluminescent-labeled biological ligands, such as immunoglobulin G (IgG) and cyclic AMP (cAMP), as the donor labels and their respective fluorescent-labeled antibodies as the acceptor labels. Patel, A., Davies, C. J., Campbell, A. K., and McCapra, F., Chemiluminescence Energy Transfer: A New Technique Applicable to the Study of Ligand-Ligand Interactions in Living Systems, *Anal. Biochem.*, 129, 162-169 (1983). A chemiluminescent compound emits light as the result of a chemical reaction. This particular energy transfer assay takes advantage of the fact that all or a portion of the light, or energy, produced by a chemiluminescent label can be transfered to a fluorescent label, such as fluorescein, where the fluorescent label is brought into close proximity with the chemiluminescent label. The proximity is caused by the specific binding reaction between a chemiluminescent-labeled ligand and its fluorescent-labeled specific binding partner.

Absorption, by the fluorescent label, of energy produced by the chemiluminescent label generally results in a decrease in light emission between about 460 and 487 nm and an increase in light emission between about 525 and 555 nm. Id. The exact wavelength ranges wherein a shift is observed will depend upon the particular chemiluminescent and fluorescent compounds selected as labels.

In a typical competitive binding assay of this type, free analyte from a test sample competes with chemiluminescent-labeled analyte for a finite amount of available fluorescent-labeled antibody. Energy transfer occurs only where the labeled analyte is bound to the labeled antibody. The amount of shift is inversely proportional to the amount of free analyte present in the test sample.

It would be advantageous to have a reagent for competitive proximity assays which would yield a direct positive correlation, rather than an inverse relationship, to the amount of analyte present in a test sample. It would also be advantageous to have reagents which exhibit improved stability characteristics for use in proximity assays. Although chemiluminescent-labeled antigens are reportedly stable for nine months, this stability requires storage at $-20°$ C. Id. It would be desirable if such a reagent were comparably stable at room temperature.

6. Prior Art Conjugation Methods

Most specific binding assays require the use of conjugates of one form or another. For example, the typical sandwich immunoassay requires the conjugation of a label, such as an enzyme or fluorescent compound, to an antibody which functions as the labeled antibody of the sandwich. Conjugates are also used in other processes including synthesis reactions.

A conjugate is simply two substances coupled together. Usually at least one of the substances is a protein. In some cases, such as with an enzyme-labeled antibody, both substances are proteins. Most proteins, as well as certain other substances, have active sites, some or all of which may be important to the ultimate desired performance of the conjugate. Examples of active sites include the active site(s) of an enzyme, the binding arms of an antibody, and the epitope(s) of an antigen or hapten. In conjugating a protein or other substance having active sites it is important to perform the conjugation; i.e., chemical modification, away from the active site.

Conjugation methods generally employ relatively harsh conditions to effect the necessary chemical modification of a protein. This can cause denaturization and/or deactivation of the protein. Moreover, these methods are nondiscriminatory in nature, seeking out a particular type of reactive site on a protein regardless of whether it occurs at or near an active site of the protein. The most common reactive sites used in protein conjugation are amino groups and carboxyl groups, although surface sulfhydryl groups are also frequently used. The random nature of these reactions poses a problem with proteins which have these particular reactive groups at or near the active site.

One method which has been suggested to alleviate the problem of harsh reaction conditions is the use of azide ($N_3$) as one member of a heterobifunctional cross-linking agent. As previously noted, heterobifunctional cross-linking agents are to be distinguished from small molecule heterobifunctional conjugates, inasmuch as the former utilize two chemically reactive groups, rather than two small molecule ligands. The azide moiety of the cross-linking agent readily converts to an activated nitrene form upon exposure to ultraviolet light. The activated nitrene can then insert into almost any chemical bond without the use of harsh reaction conditions.

Specifically, a heterobifunctional cross-linking agent employing a succinimide ester of a carboxylic acid residue as one chemically reactive group and an azide residue as the other chemically reactive group has been suggested for use in the conjugation of two proteins. Guire, P., Fliger, D. and Hodgson, J., Photochemical Coupling of Enzymes to Mammalian Cells, *Pharm. Res. Com.*, 9(2), 131-141 (1977). An excess of the cross-linking agent is initially added to a solution containing a first protein. The succinimide ester of the carboxylic acid residue binds to any amino functional group of the first protein in a nondiscriminatory manner. This reaction is carried out in the dark due to the reactive nature of the azide residue. Once the reaction between the succinimide ester and the amino groups has taken place and the excess cross-linking agent is eliminated, a second protein is added, and the reaction mixture is exposed to ultraviolet light which converts the azide residue to nitrene. The nitrene is extremely reactive and, in this reactive form, will insert into any chemical bond of the second protein which is readily available to the activated nitrene end of the cross-linking agent. Although relatively mild reaction conditions are encountered in this second phase of the conjugation, relatively good recovery is achieved only where the first protein does not have a reactive free amino group critical to the active site of the protein. In any event, excellent recovery is precluded by the random nature of the nitrene insertion.

Yet another conjugation method addresses the issue of site specificity, but fails to alleviate the problem of harsh reaction conditions. This method targets the polysaccharide moiety of a protein for use as the conjugation site. Most proteins contain a surface polysaccharide group which is located at a site distant from the active site of the protein, making the polysaccharide moiety an ideal location for modification. The active site(s) of a protein does not contain these polysaccharide moieties. Thus, there is little danger of chemically modifying the active site(s). Modification of a polysaccharide moiety generally involves the reactivity of the cis-diol group of the sugar. Traditionally, however, this has entailed relatively harsh reaction conditions requiring: (1) periodate oxidation of the cis-diol group; followed by, (2) reductive amination. These harsh reaction conditions usually lead to denaturation of the protein.

It would be desirable to have a method for conjugating proteins which would not only proceed under relatively mild reactive conditions, but which would also take place in a discriminatory manner such that the reactive site of a protein would remain unmodified.

SUMMARY OF THE INVENTION

The present invention provides novel tridentate conjugates generally applicable for use in analytical methods as well as in the preparation of reagents for various purposes. The tridentate conjugates are trifunctional conjugates having three chemical moieties, or tridentate members, attached together through an appropriate spacer moiety. At least two of the tridentate members are small molecules. One or more of the tridentate members may be the ligand portion of a small molecule ligand: specific binding partner pair. In one embodiment, the tridentate members and spacer moiety are selected and arranged so that the binding of a macromolecule to one of the three tridentate members sterically inhibits the binding of another macromolecule to one of the remaining tridentate members. In another embodiment, one of the tridentate members is selected to act as a guide, in other words, to bind to a first location on a macromolecule such that, while the guiding tridentate member is bound, one of the remaining tridentate members will bind to the same macromolecule in a second location proximate to the first location. Subsequent to the binding of the latter tridentate member, the binding of the former, i.e., guiding, tridentate member may be reversed.

DETAILED DESCRIPTION OF THE INVENTION

Figure 1:
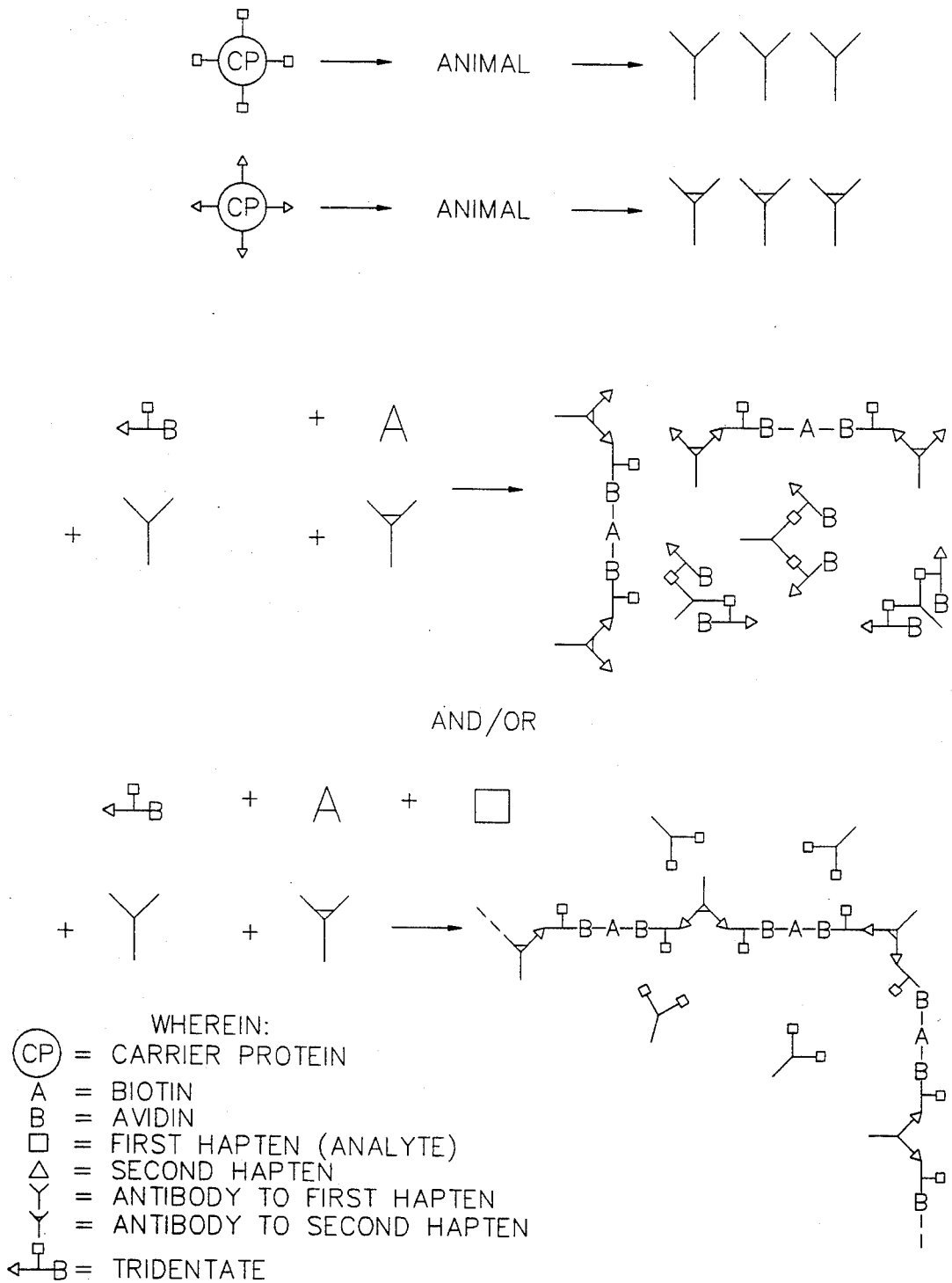
FIG. 1 depicts a nephelometric immunoassay procedure using a specific embodiment of the present invention.

In the context of this disclosure, the following terms shall be defined as follows unless otherwise indicated:

Ligand: the smaller molecule in a complex or conjugate in which the smaller molecule specifically binds to a larger molecule or substance. The ligand may be naturally occurring or artificially manipulated.

Specific binding partner: the larger molecule or substance in a complex or conjugate in which the specific binding partner specifically binds to a smaller molecule. The specific binding partner has a specific binding affinity for the ligand to the exclusion of other substances. The specific binding partner may be naturally occurring or artificially manipulated. Antibody fragments, for example, are included within this definition.

Ligand analog: an analog of the ligand molecule that can bind to the specific binding partner of the ligand in much the same manner as the ligand. The term "ligand" as used herein is generally intended to embrace ligand analogs and immunochemically equivalent materials.

Small molecule ligand: a ligand of less than about 7,000 Daltons in size. The small molecule ligand may be a piece or fragment of a larger ligand, such as an antigen. Where the small molecule ligand is an antigen fragment, the fragment should be recognized by antibody to the antigen with the same or similar degree of affinity that the antibody would have for the whole antigen.

Small molecule: a chemical moiety of less than about 7,000 Daltons in size.

Chemically reactive group: a chemical moiety which is capable of forming a covalent bond with another chemical moiety.

Proximity label: one of two or more small molecules which are capable of generating signal when located proximately to each other.

Macromolecule: a larger molecule or substance of greater than about 10,000 Daltons in size.

Simultaneous binding: the ability of two or more tridentate members of the same tridentate to be bound to macromolecules at the same time. The binding of one macromolecule may in fact occur prior in time to the binding of another macromolecule.

Novel tridentate conjugates, or tridentates, are provided in accordance with the present invention. What is meant by tridentate conjugate is a trifunctional conjugate having three chemical moieties, or tridentate members, attached through an appropriate spacer moiety. Generally, two or more of the tridentate members are small molecules which are capable of interacting with a macromolecule. These small molecule members may interact with the same or a different macromolecule. As many as three of the tridentate members may be small molecule ligands. Specific examples of small molecule ligands which may be used in the tridentate of the present invention include: hormones such as insulin, steroid hormones, and thyroid hormones; vitamins such as $B_{12}$, folic acid, and biotin; haptens such as 1-substituted-2,4-dinitrobenzene (also known as dinitrophenol, or DNP) and drugs, including the bronchodilator theophylline; and polypeptides such as antigen fragments. Representative small molecule ligand:specific binding partner pairs are: hormone:receptor; hapten:antibody; polypeptide:antibody, oligonucleotide:complementary DNA or RNA; biotin:avidin; vitamin $B_{12}$:intrinsic factor; folate:-folate binding protein; and, insulin:anti-insulin.

The tridentate members are selected and arranged on the tridentate conjugate through a selected spacer moiety. This enables the tridentate members to operate pursuant to certain steric properties which are imparted to the tridentate by the particular spacer moiety selected. In the interest of clarity, the tridentate members will frequently be referred to as a first tridentate member, a second tridentate member, and a third tridentate member. The second tridentate member is situated between the first and third tridentate members. The spacer moiety may be generally depicted as a "Y" with each arm of the "Y" plus the tail being attached to one of the three tridentate members. In other words, a portion of the section of the spacer connecting the first and second tridentate members will be common to the section of the spacer connecting the first and third members, and so forth. See, for example, FIG. 7. Thus, the first tridentate member is also "between" the second and third members, and the third tridentate member is "between" the first and second members.

The Preferred Embodiments

1. Steric Hindrance

In one embodiment of the present invention, the tridentate is designed to employ the phenomenon of steric hindrance, or inhibition. This embodiment may be referred to as the steric hindrance embodiment. In this first embodiment, at least two of the tridentate members are preferably small molecule ligands which each bind to a different macromolecular specific binding partner. The tridentate members are selected and arranged so that the binding of one of the tridentate members to its specific binding partner sterically inhibits the binding of another tridentate member to its corresponding specific binding partner. For the sake of convenience, the second tridentate member is designated as the "modulating" member; i.e., the tridentate member responsible for creating steric hindrance when bound to a macromolecule. The binding of a macromolecule to the second member (modulating) member of the tridentate prevents the simultaneous binding of the first and/or third tridentate members to their corresponding macromolecules, usually their respective specific binding partners. There are any number of practical applications of the steric hindrance embodiment of the invention, particularly in the area of competitively modulated immunoassays.

Where the tridentate members are all small molecule ligands which bind to macromolecular specific binding partners, the section of the spacer moiety connecting the first and third tridentate members must be of sufficient length to allow simultaneous binding of the first and third tridentate members to their respective specific binding partners in the absence of binding by the modulating second tridentate member to its specific binding partner.

The positioning of the second member on the spacer moiety is likewise critical. The section of the spacer moiety connecting the first and second tridentate members and/or the section of the spacer moiety connecting the second and third tridentate members must be short enough to effect modulation when the second member is bound to its specific binding partner. The binding of a macromolecule to the second tridentate member may sterically inhibit the respective binding of the first tridentate member, the third tridentate member, or both the first and third tridentate members, depending on how proximately the second tridentate member is located to either of the remaining tridentate members. The binding of a macromolecule to at least one of the remaining members must be inhibited for modulation to occur.

Where three small molecule ligands are employed as the tridentate members, the steric hindrance embodiment of the invention may generally be universally used in competitively modulated immunoassays. For this reason, this particular embodiment may be referred to as the universal tridentate. Where the specific binding partners for the first and third tridentate members are polyvalent, this group of immunoassays can be expanded to include NIIA's. The tridentate is particularly useful in competitively modulated assays where the analyte of interest is a hapten, or analog thereof, with a molecular weight between about 100 and 1500 Daltons.

Where the tridentate is generally intended for use in a competitive type of modulated assay, the second tridentate member is selected to be identical or analogous to the analyte of interest. It is necessary that the second tridentate member be able to compete with free analyte for the same specific binding partner, usually an antibody. This antibody, otherwise referred to as analyte-specific antibody, is present in limited quantity. The first and third tridentate members are preferably selected to be the ligand portion of a small molecule ligand:specific binding partner pair which is different from the analyte of interest. The first and third tridentate members may be the same small molecule ligand, or they may be different small molecule ligands. In one preferred embodiment, both the first and third tridentate members are biotin moieties.

A. Nephelometric Assays

As indicated, this particular application of the steric hindrance embodiment of the tridentate may be used in a modulated NIIA where the specific binding partners for each of the first and third tridentate members are polyvalent. Each such polyvalent specific binding partner is capable of linking up with at least two tridentates through the corresponding small molecule ligand member of each tridentate conjugate to which it binds. In this way, in the absence of modulation (macromolecular binding to the second member), large aggregates of sufficient length to fold into scattering centers can be formed. The binding of specific binding partner, usually analyte-specific antibody or macromolecular antibody fragment, to the second member position of the tridentate modulates complexing by preventing the simultaneous binding of the first and/or third tridentate members to their respective polyvalent specific binding partners. The presence of free analyte, contributed by a test sample, ties up available analyte-specific antibody, thus decreasing modulation and increasing complex formation.

A NIIA using a particular preferred tridentate of the present invention is shown in FIG. 1. In this representation, macromolecular binding to the second member sterically inhibits the binding of both the first and third tridentate members to their specific binding partners. The first tridentate member is biotin. Biotin specifically binds to the polyvalent avidin molecule, having a molecular weight of around 63,000 Daltons. The second tridentate member is a first hapten, such as theophylline, which is identical to the analyte of interest. The third tridentate member is a second hapten different from the analyte of interest, such as DNP. The second and third members specifically bind to their respectively polyvalent antibodies, each having a molecular weight of about 150,000 Daltons. These antibodies are produced by injecting into an animal a carrier protein conjugated to a plurality of either first or second hapten molecules, as is shown in FIG. 1A.

Where the tridentate is contacted only with antibody to the second hapten and avidin, simultaneous binding of the first and third members will occur. Where, however, antibody to the first hapten (analyte) is also added to the reaction mixture, complexing will be inhibited, due to binding of this antibody to the modulating second member position of the tridentate. In this case, binding of the analyte-specific antibody to the second tridentate member sterically inhibits the simultaneous binding of the corresponding specific binding partners to both the first and third members, as is shown in FIG. 1B. Where free analyte (first hapten) from a test sample is present, analyte-specific antibody is diverted away from the second member position of the tridentate by the free analyte, thereby decreasing modulation and increasing complex formation, as is shown in FIG. 1C. This results in a positive correlation of increased signal, or complex formation, with increasing concentrations of free hapten.

In addition to the suggested biotin-theophylline-DNP tridentate, other tridentates, including biotin-theophylline-biotin, will work equally well in a NIIA for theophylline or theophylline-amine where theophylline is also the second (modulating) member of the tridentate. Examples of other drugs which can also be assayed effectively in a competitively modulated assay such as a NIIA, using the tridentate of the present invention, include therapeutic drugs such as digoxin, disopyramide, lidocaine, procainamide, propranolol, quinidine, amykamycio, chloramphenicol, gentamicin, kanamycin, netilmycin, tobramycin, tricyclic antidepressants, ethosuximide, phenobarbital, phenytoin, primidone, valproic acid, acetaminophen, acetylsalicylic acid, methotrexate, and drugs of abuse such as morphine, codeine, and heroin, and their metabolites. Examples of other haptens which can be assayed using the tridentate conjugate include DNP, 1-substituted-4-hydroxy-2-nitrobenzene, and 4-substituted-2-nitro-trialkylanilinium salts.

Unlike prior art developer antigens, the tridentate is a stable, chemically defined organic compound which enjoys prolonged shelf life, and does not require the expensive purification and characterization procedures inherent with the prior art conjugates. The tridentate of the present invention also yields improved sensitivity, due to the fact that complexing is based on the competition of only one moiety on the tridentate, namely the second (modulating) member with free analyte, rather than the competition of the plurality of hapten moieties conjugated to the typical prior art developer antigen. The prior art problem of nonproductive binding is also eliminated.

B. Proximity Assays

This same universal tridentate can generally be applied to other types of competitively modulated assays, including those using proximity labels. These assays are particularly effective in detecting the same group of analytes previously mentioned. In these assays, the second tridentate member again acts as the modulator. One proximity label is attached to the macromolecular specific binding partner for the first member of the tridentate conjugate. The other proximity label is attached to the macromolecular specific binding partner for the third member of the tridentate conjugate. Where the two macromolecules simultaneously bind to the first and third tridentate members, a measurable reaction takes place between the two proximity labels. Where specific binding partner to the second tridentate member; i.e., analyte-specific antibody, binds to the modulating second member of the tridentate, at least one of the labeled macromolecules will be sterically inhibited from simultaneously binding to either the first or third tridentate member, thus reducing signal.

The section of the spacer moiety connecting the first and third tridentate members of the universal tridentate must again be of sufficient length to allow the simultaneous binding of the labeled macromolecules. However, at the same time, the length of this section of the spacer must be sufficiently short to bring the labels into close enough proximity to obtain a measurable reaction. The length required to achieve the required proximity will vary to some degree with the particular type of proximity assay chosen, but is, in general, relatively long. For example, energy transfer between proximity labels can ordinarily occur at lengths of about 18 Å to about 70 Å.

In an enzyme channeling assay, the first enzyme is preferably attached to the specific binding partner of either the first or third tridentate member, with the second enzyme being attached to the corresponding specific binding partner of the remaining first or third member. Good enzyme pairs for use in an enzyme channeling assay include glucose oxidase and peroxidase, and hexokinase and glucose-6-phosphate dehydrogenase. The second tridentate member is identical or analogous to the analyte of interest, and competes with free analyte from a test sample for a limited amount of antibody to the analyte of interest. In the absence of binding by the analyte-specific antibody to the second tridentate member, macromolecules carrying the first and second enzymes will be able to simultaneously bind to the first and third tridentate members such that the product of the first enzyme can be converted by the second enzyme before the product escapes into bulk solution.

Where, however, little or no free analyte is contributed by the test sample, analyte-specific antibody will be able to bind to the second tridentate member, sterically blocking the binding of the respective enzyme-labeled macromolecules to the first and/or third tridentate members, thereby modulating enzyme channeling; i.e., reducing signal. The greater the amount of analyte from a test sample, the less antibody will be able to bind to the tridentate. Modulation will decrease, and enzyme channeling will increase, as will the amount of signal generated.

Similarly, in an energy transfer assay, the donor label is preferably attached to the specific binding partner of either the first or third tridentate member, with the acceptor label being attached to the corresponding specific binding partner of the remaining first or third member. As with the NIIA and enzyme channeling methods, the second tridentate member is identical or analogous to the analyte of interest. The second tridentate member competes with free analyte from a test sample for a limited amount of antibody to the analyte of interest. The greater the amount of antigen contributed by a test sample, the more analyte-specific antibody will be diverted from its modulating position wherein it is bound to the second tridentate member. Lesser amounts of analyte result in less energy transfer and, therefore, less signal.

Several donor-acceptor pairs are available for use in energy transfer assays employing the tridentate of the present invention. The donor label should generally be a compound which absorbs external energy and emits light energy. Examples of good donor labels include fluorescent compounds, scintillation dyes, and chemiluminescent compounds such as isoluminol and acridin ester. Acceptor labels are usually fluorescent compounds which can absorb the energy emitted by the donor and, in turn, emit fluorescence at a wavelength longer than that of the donor's emitted light energy. Preferably, acceptors should have a good fluorescence efficiency. Good acceptor labels include fluorescein, rhodamine, fluorescent lanthanide chelates, and fluorescent tin or zinc derivatives of protoporphyrins. Rhodamine is a particularly good acceptor label, because it is capable of absorbing energy emitted by a donor over a wide spectrum of wavelengths. Examples of good donor:acceptor pairs are: isoluminol:fluorescein, acridin ester: fluorescein, and fluorescein: rhodamine.

In yet another preferred application of the steric hindrance embodiment of the invention, a tridentate other than the universal tridentate is utilized in competitively modulated assays employing proximity labels. In these assays, a tridentate is used wherein only two of the tridentate members are small molecule ligands. One of these small molecule ligand members is preferably the second, or modulating, member of the tridentate which typically competes with free analyte for a limited amount of analyte-specific antibody. The other small molecule ligand member binds to its macromolecular specific binding partner which has been conjugated to a first proximity label. Where analyte-specific antibody is bound to the second member position, the labeled macromolecule is sterically inhibited from binding to the same tridentate.

Figure 11:
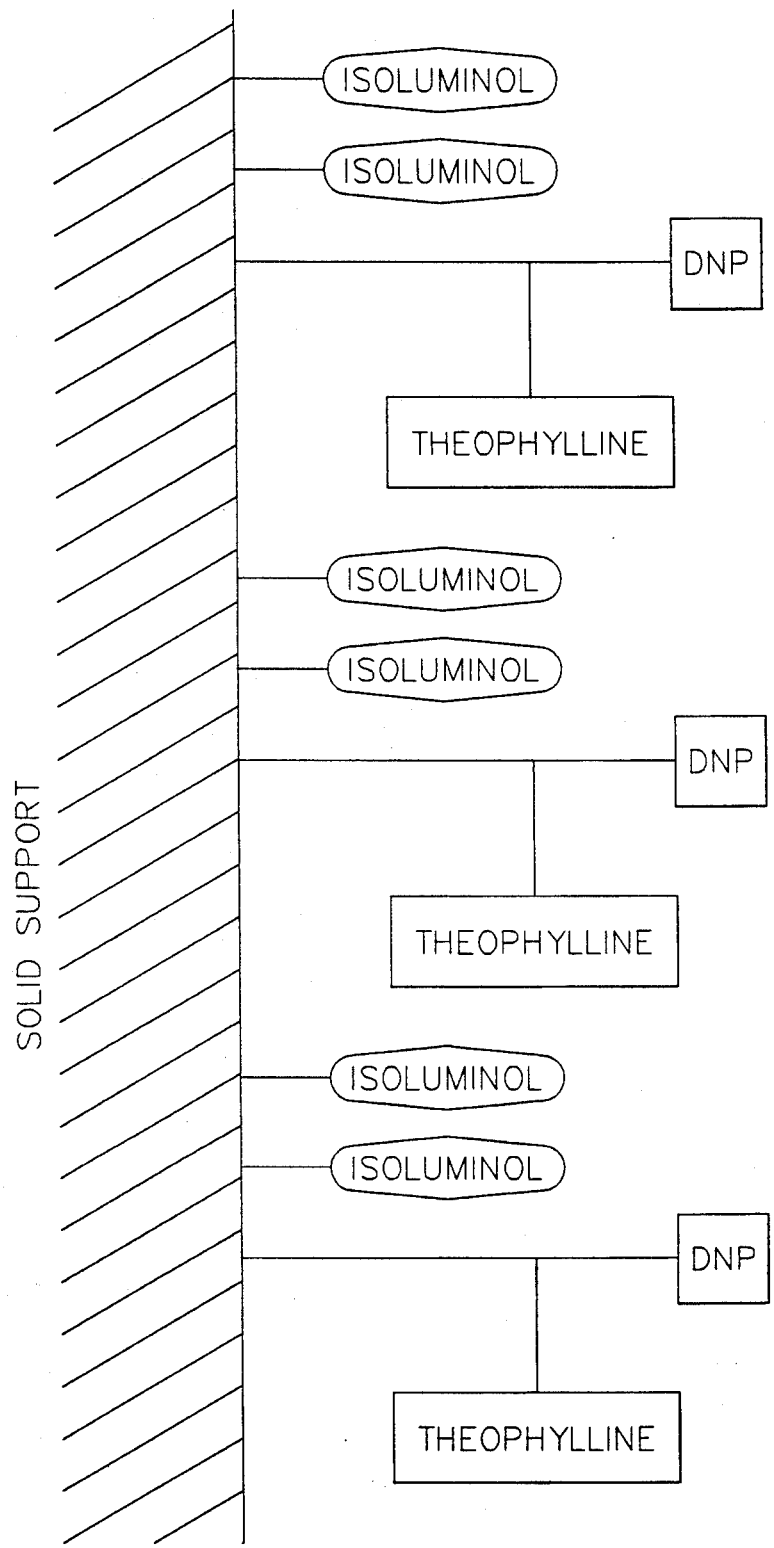
FIG. 11 illustrates a series of identical tridentates intended for use in an energy transfer assay using the steric hindrance embodiment of the present invention wherein one of the tridentate members is a solid support conjugated to a plurality of proximity labels.

In the absence of modulation by the second member, the first proximity label is preferably brought into proximity with a second proximity label in one of two ways: (1) the second proximity label is conjugated directly to the tridentate as a tridentate member; or, (2) a plurality of second proximity labels is attached to a large macromolecule or solid support, which is conjugated directly to the tridentate as a tridentate member. In the latter instance, particularly where one of the tridentate members is a solid support, a multiplicity of tridentates may share the same solid support member, as is shown in FIG. 11. The extent to which the specific binding partner containing the first proximity label is able to bind to the tridentate controls the extent of signal generated. Free analyte from a test sample increases this signal by diverting analyte-specific antibody away from its modulating position on the tridentate.

The tridentate of the present invention provides the same general advantages in proximity assays as in nephelometric assays. The defined chemical nature of the synthesized organic tridentate alleviates many of the problems typically encountered in dealing with the naturally occurring proteinaceous substances which form the basis for most prior art reagents. The tridentate does not require the expensive isolation and characterization procedures of prior art reagents, and exhibits a much longer shelf life than its prior art counterparts. The same haptens and drugs may be conveniently assay using these methods as may antigens where antigen fragments can be effectively employed as the modulating tridentate member.

2. Targeted Labeling

Another embodiment of the present invention utilizes a tridentate which is designed to employ a different steric phenomenon which may be referred to as region-specific labeling, or targeted labeling. At least two of the members of this tridentate are small molecules. These two small molecule members are capable of binding to the same macromolecule, and at least one of these two small molecule members is a chemically reactive group. The third tridentate member may be a small molecule ligand. It may also be a small molecule other than a small molecule ligand, or even a macromolecule. The targeted labeling embodiment of the tridentate can be advantageously used where it is desired to bind a small molecule ligand or other third tridentate member to a targeted site or sites on a particular macromolecule. This third tridentate member may act as a label, tracer, or reporter group. It may also act as a solid support such as where the third tridentate member is a macromolecule. Biotin, for example, may be used as a small molecule ligand label. Radioactive compounds such as $I^{125}$ are a good example of small molecule tracers. Enzymes are good macromolecular labels.

In general principle, the binding of a first small molecule tridentate member restricts the binding of a chemically reactive second small molecule member to a particular region on the same macromolecule. The small molecule tridentate member responsible for locating and initially binding to the targeted site on the macromolecule may be either a chemically reactive group or a small molecule ligand and is referred to as the guiding tridentate member. The small molecule tridentate member whose binding is thus restricted to the vicinity or region on the same macromolecule to which the guiding member has bound is referred to as the reactive tridentate member. The reactive member must be a chemically reactive group. The third tridentate member may be conveniently referred to as the "intended label", even where the third member is, in fact, an intended solid support. Preferably, the length of the section of the spacer moiety connecting the guiding member and the reactive member will be relatively short, while that connecting the reactive member and the intended label will be relatively long.

The targeted labeling embodiment of the present invention is of particular use in the conjugation of intended labels to proteins such as proteoglycans, lipoproteins, enzymes, antibodies, and receptors. As mentioned, most proteins contain a polysaccharide or sugar moiety at a location distant from the active site of the macromolecule. Proteins containing such a polysaccharide or sugar moiety may be referred to as glycosylated proteins. Unlike the prior art methods, the tridentate is capable of targeted modification at the polysaccharide moiety of a protein without incurring the harsh reaction conditions and nonspecific binding that can denature the protein.

For example, where the tridentate is to be used to accomplish the targeted labeling of a protein, the tridentate members are preferably selected as follows: (1) the guiding member is a phenylboronic acid residue; (2) the reactive member is a nitrophenylazido residue; and, (3) the remaining tridentate member is the intended label, such as biotin. The substituted boronic acid group of the guiding member specifically seeks out and reacts with the cis-diol group of the sugar moiety of the protein to form a relatively weak boronic ester complex, or bond. This reaction is carried out in the dark. After elimination of the excess of the tridentate conjugate, the reaction mixture is then exposed to ultra-violet light, which activates the azide group of the reactive member to nitrene. The nitrene then inserts into any chemical bond within the vicinity of the previously bound guiding member. This insures a permanent bond away from the active site of the protein. Subsequent release of the guiding member, such as through hydrolysis of the boronic ester bond due to pH changes, does not impair the functional utility of the tridentate conjugate. The third member is attached to the protein through a permanent bond. The reaction is specific and the reaction conditions are mild.

Synthesis of the Tridentate Conjugate

1. Generally

The synthesis of the tridentate is relatively simple once the ultimate use of the tridentate is determined, and the tridentate members are selected. These determinations, in turn, dictate the size and configuration of the spacer moiety.

Where the tridentate is intended for use in a modulated assay, such as a NIIA, enzyme channeling, or energy transfer assay, the tridentate members will preferably be selected as suggested above. Where use in other modulated assay methods is intended, the tridentate members will be selected in a similar manner. In other words, the second tridentate member will preferably be identical or analogous to an analyte of interest, and at least one of the first and third members will preferably be a different ligand selected from small molecule ligand:specific binding partner pairs. The remaining member will ordinarily be another small molecule ligand, a proximity label, or a large macromolecule or solid support.

Where the targeted labeling embodiment is intended, such as in the specific modication of a macromolecule, the guiding member is selected to be either a small molecule ligand or a chemically reactive group capable of selectively binding to a targeted site or sites on a designated macromolecule. The reactive member is selected to be a chemically reactive group capable of permanently binding to a location on the same macromolecule proximate to the location at which the guiding member has bound. The third tridentate member is ordinarily selected to be a label, tracer, or reporter group, which may be a small molecule, a small molecule ligand, or a macromolecule, or a solid support, which is typically a macromolecular substance.

The tridentate conjugate is generally built around a starting spacer moiety, with each of the tridentate members being linked to each other through attachment onto the spacer moiety. There are many methods known in the art for linking together members of a bifunctional conjugate through spacer moieties. See, for example, U.S. Pat. No. 4,134,792, U.S. Pat. No. 4,238,565, and Green, N. M., Konieczny, L., Toms, E. J., and Valentine, R. C., The Use of Bifunctional Biotinyl Compounds to Determine the Arrangement of subunits in Avidin, *Biochem. J.*, 125, 781-791 (1971). These methods generally employ typical condensation, addition, and substitution reactions between the reactive groups of two different organic compounds which may or may not have been activated prior to conjugation. The same or similar methods may ordinarily be applied to attach the tridentate members to the selected spacer moiety as is more particularly set forth in Example 4 which follows.

The particular chemical composition of the spacer moiety will depend, to some extent, on the nature of the chemical sites available on the respective tridentate members for attachment to the spacer moiety. It will also depend on the availability of organic materials for use as the starting spacer moiety. Typical heteroatoms, including nitrogen, oxygen, sulfur, and phosphorous, may be used in the spacer moiety in addition to carbon atoms. Generally, the spacer moiety will be aliphatic, although aromatic groups may be involved. In the typical divalent chain, where single bonds employing carbon, nitrogen, or oxygen are incorporated into the spacer moiety, each such atom can be expected to increase the spacer moiety length by about 1.2 to 1.5 Å.

The precise method used to link the tridentate members together, through the spacer moiety, is not critical. What is important is that the tridentate members retain their ability to function effectively in their ultimate intended use following synthesis of the tridentate. For example, a small molecule ligand member must retain the ability to bind to its specific binding partner. This consideration may affect the exact chemical site chosen for connection to the spacer moiety. Ordinarily it is desired to maximize the exposure of the active site or sites of the particular tridentate member which allows for; e.g., a specific binding reaction, to occur.

2. Determination of Spacer Length Requirements

The required spacer length connecting each tridentate member to each other tridentate member must be determined before the tridentate can be synthesized. For example, where a tridentate employing three small molecule ligands is intended for use in a modulated assay, the minimum spacer length between the first and third tridentate members must ordinarily be determined as an initial step. This minimum spacer length establishes the point at which simultaneous binding of the first and third members to their respective specific binding partners can be achieved in the absence of modulation. Below this point, there will be no simultaneous binding.

There are a number of methods known in the art for determining the minimum spacer length required to obtain simultaneous binding of two members of a homobifunctional conjugate to their respective macromolecular specific binding partners. See, for example, Larsson, P. O., and Mosbach, K., Affinity Precipitation of Enzymes, FEBS Letters 98(2), 333-338 (1979), and Green, N. M., Konieczny, L., Toms, E. J., and Valentine, R. C., The Use of Bifunctional Compounds to Determine the Arrangement of Subunits in Avidin, *Biochem. J.*, 125, 781-791 (1971). These same methods can be used to determine the minimum spacer length required between the first and third tridentate members to achieve the same type of simultaneous binding. Specifically, a series of homologs of bifunctional conjugates of various spacer lengths, generally containing only the first and third tridentate members, are synthesized and subsequently analyzed to determine the spacer length at which simultaneous binding is first observed.

The action of simultaneous binding is ordinarily detected by the production of measurable signal which is generated pursuant to the simultaneous binding reaction. One such convenient method for determining minimum spacer length is through the use of standard nephelometric or turbidimetric procedures which detect scattering complexes as a measure of simultaneous binding. These methods require the availability of polyvalent macromolecules to bind to each of the members of the bifunctional conjugate and are useful even where the formation of complexes large enough to form scattering centers is not the ultimate intended use of a particular tridentate. Specifically, bifunctional conjugates which vary only with respect to spacer length (otherwise known as homologs) are brought into contact with the respective multivalent specific binding partners for each member.

A bifunctional conjugate having biotin and theophylline as the two conjugate members may, for example, be used for a study to detect minimum spacer length. Biotin contains a biologically active alicyclic ring and a short 5-carbon aliphatic tail. In this case, spacer length may be conveniently measured from the biologically active ring structure, with the aliphatic tail being incorporated into the spacer. Homologs of the bifunctional conjugate are prepared and brought into contact with avidin and anti-theophylline antibody. Nephelometric measurements are then taken to detect the amount of complexing, if any. Minimum spacer length is the point at which measurable nephelometric signal is first observed. Optimal spacer length is ordinarily severl bonds longer. The amount of complex formation will ordinarily reach a plateau within several carbon atoms or heteroatoms of the minimum spacer length. It is generally desirable to choose a spacer length near this plateau.

The optimal minimum spacer length does not vary significantly with different proportions of bifunctional conjugate, avidin, and antibody. Moreover, the same minimum spacer length data will generally apply where haptens other than theophylline are used as one of the members of a hapten-biotin bifunctional conjugate, although some slight variation may be observed. Where small molecule ligands other than biotin are incorporated as one of the bifunctional conjugate members, a somewhat greater degree of variation can be expected, due to the greater variation in the size and shape of the different specific binding partners for these ligands as compared to avidin. Consequently, separate homolog studies may be required in some cases to optimize minimum spacer length data. Nevertheless, the study of a theophylline-biotin conjugate, or similar small molecule bifunctional conjugates will provide sufficient optimal minimum spacer length data to at least establish the starting point for the successful synthesis of any number of tridentate conjugates of the steric hindrance embodiment.

The bifunctional conjugates used to determine minimum spacer length may be synthesized by any one of a number of known prior art methods, as previously indicated. It is preferred that the selected process include the insertion of a compound which is one in a series of homologs in a particular class of compounds. For example, the alkanediamine ($NH_2$—$(CH_2)_N$—$NH_2$) class of compounds contains ethanediamine (N=2), propanediamine (N=3), butanediamine (N=4), pentanediamine (N=5), and so forth. Where the synthesis process includes the insertion of one of these homologs, other homologs may be easily substituted to vary the chain length of the spacer connecting the two members of a bifunctional conjugate.

Homologs of two different theophylline-biotin bifunctional conjugates may, for example, be prepared in this way. In the interest of clarity, these two bifunctional conjugates are referred to herein as bifunctional conjugate I and bifunctional conjugate II. Bifunctional conjugate II differs primarily from bifunctional conjugate I in having a carbon atom adjacent to the theophylline moiety rather than the nitrogen atom located adjacent to the theophylline moiety in bifunctional conjugate I.

Initially, primary amine derivatives of theophylline may be prepared from commercially available starting theophylline derivatives as a first step in the synthesis process. Other methods may be used to prepare primary amine derivatives of other haptens. Where bifunctional conjugate I is prepared, an excess of a diamine is refluxed with the starting derivative 8-bromotheophylline. This generally takes place under a nitrogen atmosphere for a period of two to seventy-two hours, depending upon the particular diamine selected, and results in product I.

Bifunctional conjugate II is prepared from theophylline-8-butyric acid as the starting theophylline derivative and demonstrates the need for activation prior to achieving the desired condensation reaction. Specifically, carbonyldiimidazole (CDI) and N-hydroxysuccinimide (NHS) are used to activate the carboxylic group of the starting derivative theophylline-8-butyric acid before the selected diamine can be inserted. Activation is carried out by dissolving theophylline-8-butyric acid in anhydrous dimethylformamide (DMF), followed by heating to about 70° C. with the subsequent addition of CDI. The reaction temperature must be maintained at about 70° C., usually for approximately 15 minutes, before it is cooled back to room temperature. The NHS is subsequently added to the cooled reaction mixture and stirred overnight at room temperature. An excess of diamine may then be added to the activated reaction mixture. This results in product II.

The completion of the reaction producing the required primary amine derivative may be determined by a thin layer chromatographic (TLC) analysis of either reaction mixture I or reaction mixture II, using glass TLC plates coated with silica gel and an ultraviolet indicator.

The reaction mixtures must then be evaporated to a small volume under vacuum, with the concentrated reaction mixtures being purified by standard silica gel column chromatography using a gradient chloroform: methanol mixture. The eluted fractions containing the pure primary amine derivatives of theophylline are pooled and evaporated to dryness in a rotary evaporator. The white-yellowish crystalline solids obtained upon evaporation may be used for the next reaction without further purification. Theophylline monoamine derivatives have a molar absorptivity of about $1.9 \times 10^3$ at 295 nm in methanol.

Figure 2:
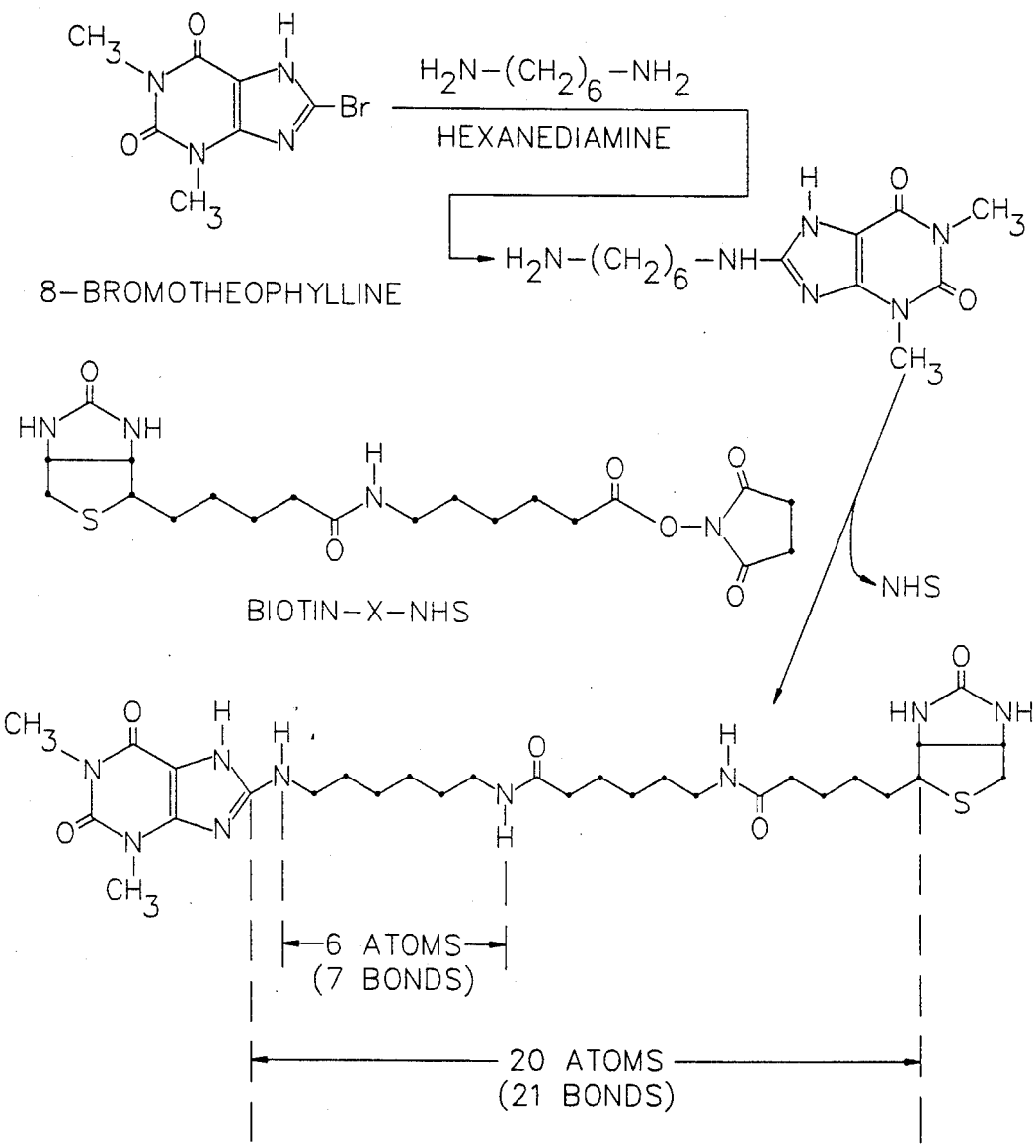
FIG. 2 schematically represents the synthesis of a bifunctional conjugate I homolog.
Figure 3:
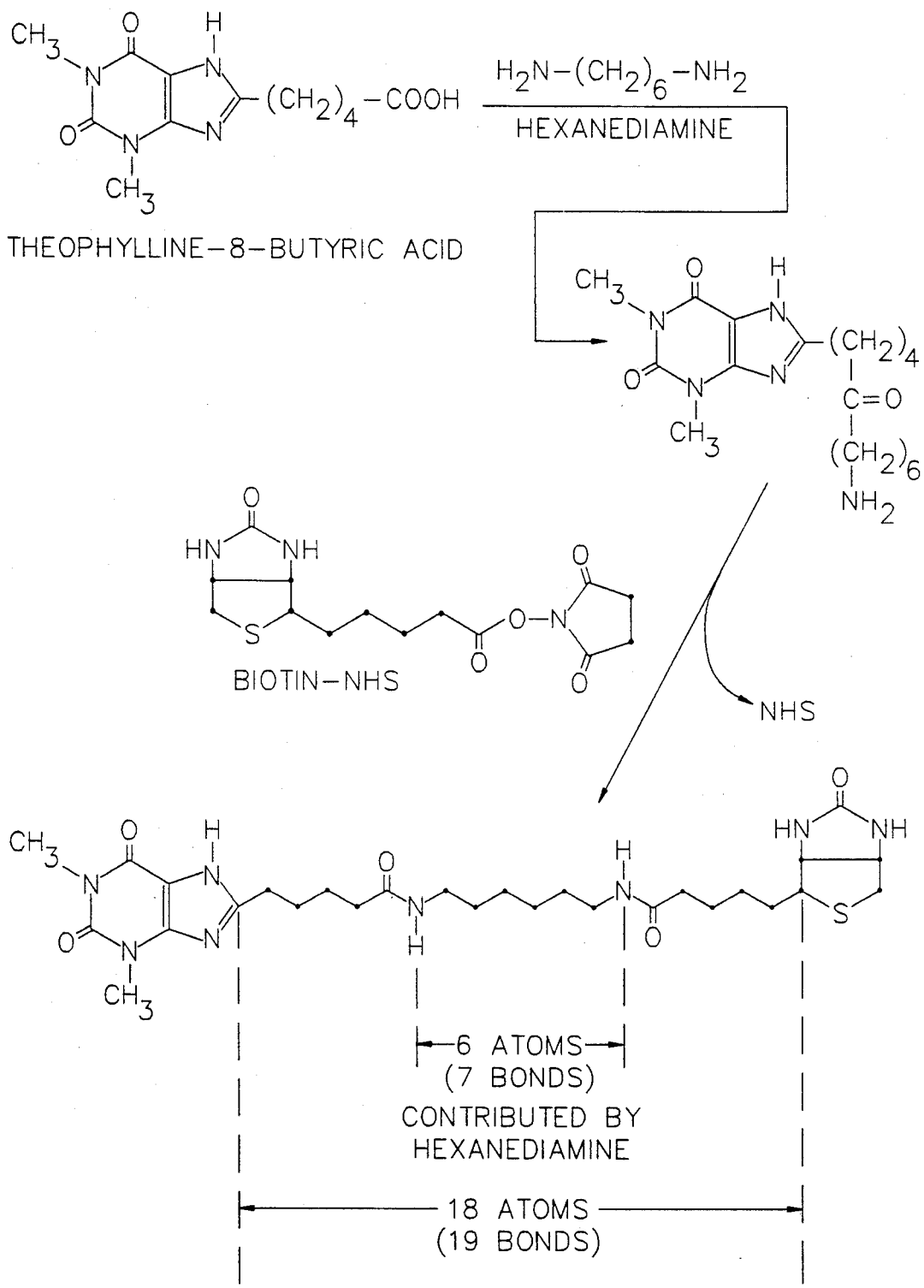
FIG. 3 schematically represents the synthesis of a bifunctional conjugate II homolog.

Biotin-theophylline conjugate I is prepared by dissolving the crystalline solids containing the primary amine derivatives of theophylline from reaction mixture I in anhydrous DMF and then mixing in the activated N-hyroxysuccinimide ester of caproamidobiotin (biotin-X-NHS), as is schematically shown in FIG. 2. Primary amine derivatives of other haptens may similarly be condensed with biotin-X-NHS or any other chemical moiety containing an activated carboxyl group. This solution is also stirred overnight at room temperature. Biotin-theophylline conjugate II is similarly prepared, with the exception that the crystalline solids containing the primary amine derivatives of theophylline from reaction mixture II are mixed with the N-hydroxysuccinimide ester of biotin (biotin-NHS), as is shown in FIG. 3. In either case, the desired products usually separate out of DMF as white, flocculent solids. The product may be collected on filter paper and purified to a single spot in a TLC test, either by preparative thin layer chromatography or by column chromatography.

Other methods which can similarly be used to determine minimum spacer length include enzyme channeling and energy transfer schemes. The same series of homologs of bifunctional conjugates used in the NIIA analysis, may be brought into contact with the respective labeled specific binding partners for each of the first and third members. These studies are similar to typical modulated assay systems, except that there is no free analyte and no modulator. Signal, generated by the proximity labels, will again begin to be observed at the minimum spacer length which allows for simultaneous binding of the labeled macromolecules, with optimal spacer length ordinarily being a little longer than minimum spacer length.

Where either the first or third tridentate member does not have a specific binding partner, spacer length between the first and third tridentate members is not as critical, because there is no requirement of simultaneous binding between these two members. For example, where one of these members is a second proximity label, a specific binding partner conjugated to a first proximity label can easily bind to its corresponding tridentate member due to the small molecular size of the second proximity label (tridentate member). Where one of the first or third tridentate members is a macromolecule to which has been conjugated a plurality of second proximity labels, there will ordinarily be some minimum spacer length requirement to enable the labeled specific binding partner to bind to its corresponding small molecule ligand member, but the minimum spacer length will be shorter than that required for simultaneous binding of two specific binding partners. In this instance, similar homolog studies can be performed wherein one member of the bifunctional conjugate homolog is the intended macromolecular tridentate member.

It should be noted that the section of the spacer moiety connecting two tridentate members is ordinarily not as straight or rigid as the spacer moiety connecting two bifunctional conjugate members. This is due, in part, to the tetrahedral spatial arrangement of the four bonds of the carbon atom ordinarily located at the hinge position of the spacer. See FIG. 7. For this reason, an increase in spacer length on the order of about 10% to 20% should ordinarily be added to the minimum optimal spacer length observed where a bifunctional conjugate employing the intended first and third tridentate members is used to approximate the simultaneous binding action of the same members in the tridentate conjugate.

The same data generated to establish minimum spacer length for simultaneous binding between two small molecule ligand members of a universal tridentate can also be used to determine the relative positioning of the second tridentate member of a tridentate intended for use in a competitively modulated immunoassay. The section of spacer moiety connecting the second member with the remaining tridentate member(s) of which modulation is desired must be less than the minimum spacer length which allows simultaneous binding. Where the tridentate members are all small molecule ligands, the distance between the first and third tridentate members will be longer than the distance from the second (modulating) member to the first and/or third members, depending on which of the remaining members is desired to be modulated.

In the targeted labeling embodiment, the minimum spacer length requirement is between the intended label and the targeted macromolecule. Where this member is a small molecule ligand, the length of the section of the spacer moiety connecting the intended label to the reactive member must be of a sufficient length to enable the attached intended label to bind to its specific binding partner without incurring steric hindrance from the targeted macromolecule. Generally, the same data establishing the minimum spacer length for simultaneous binding between two small molecule ligands or between a small molecule ligand and a macromolecule may also be used here, although some slight experimentation with homologs may be required to fully optimize results. Where the third tridentate member is also a macromolecule, like the targeted macromolecule, spacer length is not generally critical. This is particularly true, because the present invention enables targeted conjugation such that the active site of e.g., an enzyme, can be specifically located away from the site of conjugation to; e.g., a solid support.

3. Building the Tridentate Conjugate

The three tridentate members may generally be conjugated together using traditional organic synthesis techniques known in the art. The tridentate of the present invention, however, requires the incorporation of a carefully selected spacer moiety in order to control the desired functional attributes of the tridentate. Consequently, it has been found that it is preferable to begin synthesis of the tridentate with a starting spacer moiety around which the remainder of the tridentate is built. Various sections of the starting spacer moiety may be lengthened, as desired, during the synthesis process.

It is preferred that the starting spacer moiety be an organic molecule having three chemical functional groups which can be suitably and individually derivatized. More preferably, the three chemical groups will all be different functional groups. Where two or more of the chemical groups are the same functional group, one or more of these same chemical groups must be capable of: (1) being protected while the other identical group(s) is(are) being derivatized; and, (2) subsequently being deprotected without causing chemical modification to the remainder of the partially synthesized tridentate or to the protected functional group itself.

Typical functional groups which may be suitably derivatized include amino groups ($—NH_2$), carboxyl groups ($—COOH$) and mercapto groups ($—SH$). Amino groups and carboxyl groups react with each other to unite two molecules in a typical condensation reaction. Normally, the carboxyl group must be activated prior to the condensation reaction. Mercapto groups react with other mercapto groups as well as maleidoimidyl groups to ultimately link two molecules together via covalent bonding.

The starting spacer moiety may be a synthetic molecule, or it may be a molecule found in nature. Naturally occurring amino acids generally provide good starting spacer moieties for synthesis of the tridentate. Almost all of the naturally occurring amino acids are $\alpha$-amino acids which, by definition, contain both an amino group and a carboxyl function at the $\alpha$-carbon position of the amino acid. Some of these amino acids also have an additional functional group at the $\omega$-position, or terminal carbon, of the amino acid. Lysine, for example has a second amino group at the $\omega$-position. By contrast, there is a second carboxyl function at the $\omega$-position of glutamic acid.

Mercapto amino acids, such as cysteine, are particularly suitable for use as starting spacer moieties, because they possess three different chemical functional groups, namely, amino, carboxyl, and mercapto groups. Lysine is also a preferred amino acid for use as a starting spacer group, due to its availability and relative inexpense. Other preferred amino acids include glutamic acid, as well as other naturally occurring amino acids such as tyrosine and serine.

As noted, both lysine and glutamic acid contain two identical functional groups. In order to individually derivatize the chemical groups on these and other starting spacer moieties having two identical functional groups, one of these functional groups must be protected while the other is being derivatized. Suitable protecting groups for carboxyl functions include, for example, benzyl esters and tertiary-butyl ester groups. Where the protection of an amino group is desired, carbobenzoxy esters, benzoyloxycarbonylphthalyl, or 9-fluorenyl-methyloxycarbonyl may, for example, be used. Other protecting groups for these and other functions are known in the basic synthesis art. The protecting group must be capable of removal (i.e., deprotection) without harm to the functional group or to the rest of the tridentate.

The order in which the intended tridentate members are attached to the starting spacer moiety is ordinarily not critical. In these instances, the order of attachment will generally be mandated by considerations of convenience. In certain instances, however, such as where one of the tridentate members is a solid support conjugated to a plurality of proximity labels, the solid support member should be attached last. For example, in synthesizing the tridentate(s) shown in FIG. 11, partially synthesized tridentates (having the theophylline and DNP moieties already attached) may be conjugated to a solid support at the same time as the isoluminol proximity labels. The ratio of tridentate/proximity label can generally be controlled by the respective amounts of these compounds added to the reaction medium.

A. Cyclic Acid Anhydrides as Starting Spacer Moieties

Cyclic acid anhydrides provide particularly good starting spacer moieties, due to their ability to "self-protect" one of the two carboxyl functions generally used for attaching tridentate members to these starting spacer moieties. For example, the two carboxyl functional groups of glutamic acid appear as the anhydride function of pyroglutamic acid.

Figure 4:
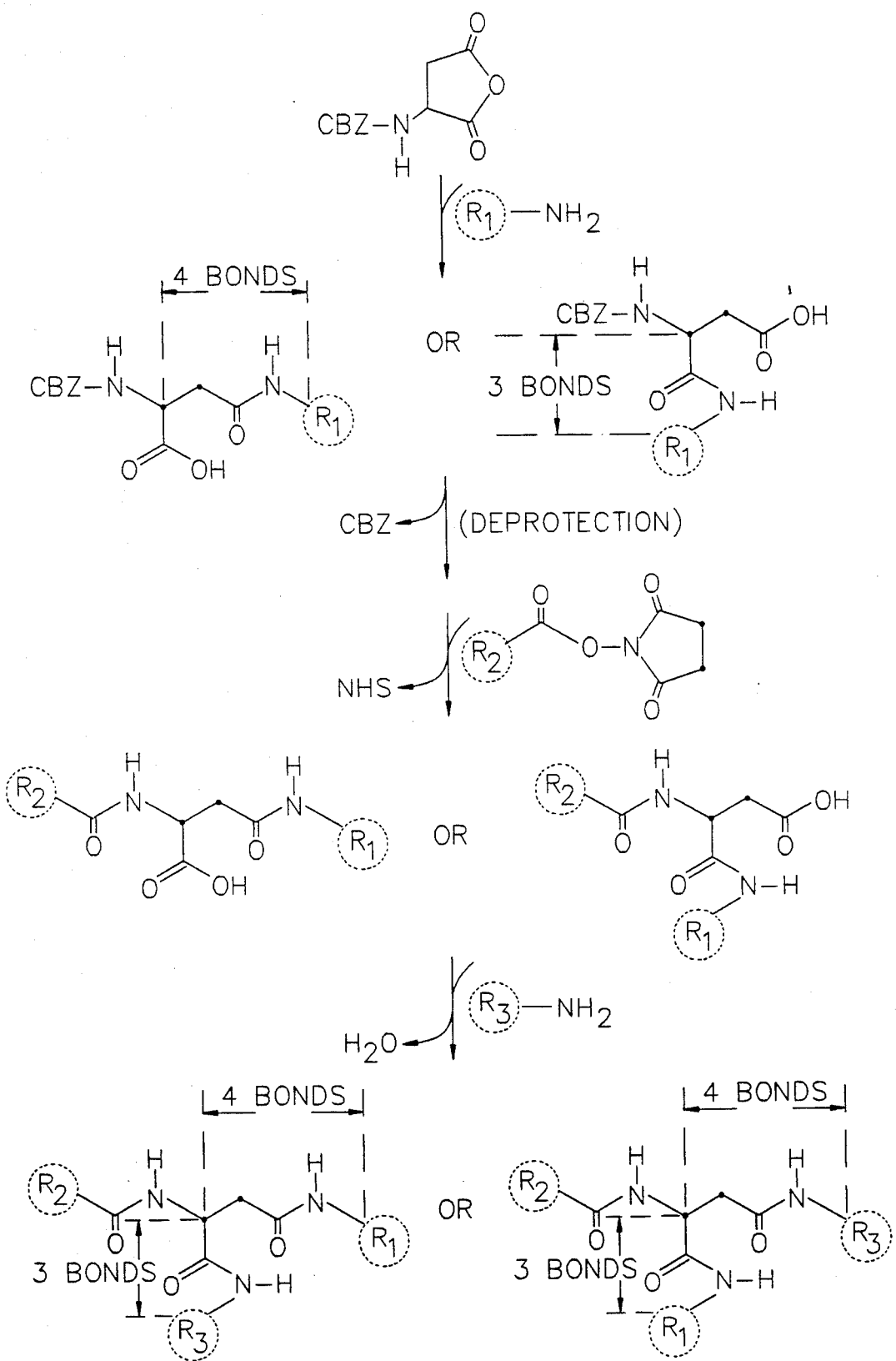
FIG. 4 schematically represents the general synthesis of a tridentate using pyroglutamic acid as the starting spacer moiety.

The primary amino group of an intended first member can react with the anhydride function of the pyroglutamic acid to yield a conjugated glutamic acid, as is shown in FIG. 4. Only one of the carboxyl groups of the anhydride function will add to the primary amino group, thus liberating the remaining carboxyl group in the form of a free carboxyl function. The free carboxyl group can later be separately derivatized through a condensation reaction with the primary amino group of another intended member. The condensation reaction can take place immediately after attachment of the first member, or, for example, following attachment of the second tridentate member to the amino function of glutamic acid, as is shown in FIG. 4. The amino function of pyroglutamic acid is preferably conjugated to a protecting group, such as a carbobenzoxy (CBZ) group, in order to prevent the amino group of pyroglutamic acid from polymerizing with the liberated carboxyl function.

Ordinarily, it is difficult to control which one of the two carboxyl groups of an anhydride function will react with a primary amine. This generally results in the formation of two different isomers, such as those shown following addition of the first tridentate member in FIG. 4. The section of the spacer moiety connecting the first member to the remaining tridentate members is one bond longer in one isomer than it is in the other; accordingly the separation distances between the members of the trifunctional conjugate can be controlled to within about one bond length. The opposite holds true with respect to the tridentate member which is attached to the liberated carboxyl function, in this case, the third tridentate member. For example, in the completed tridentate, shown in FIG. 4, the section of the spacer moiety connecting the first member to the second member is seven bonds in one isomer and six bonds in the other isomer. The opposite holds true with respect to the section of spacer moiety connecting the third member to the second member; i.e., it is six bonds long in one isomer and seven bonds long in the other. The section of the spacer moiety connecting the first and third members (the members attached through the carboxyl functions) is the same in both isomers.

Figure 5:
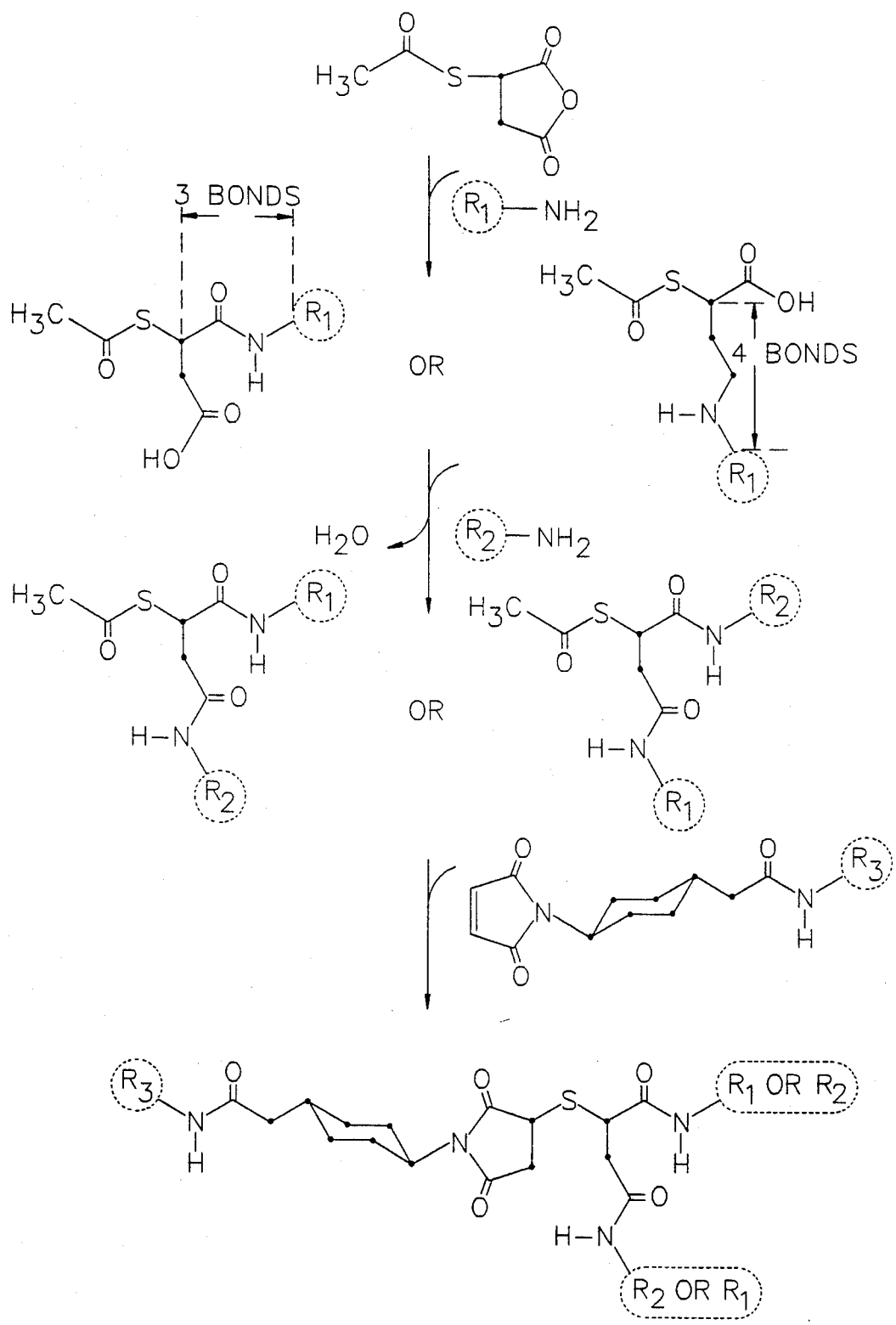
FIG. 5 schematically represents the general synthesis of a tridentate using S-acetyl-mercaptosuccinic acid as the starting spacer moiety.

Another useful cyclic anhydride is S-acetylmercaptosuccinic anhydride. The primary amino group can react with the anhydride function of S-acetylmercaptosuccinic anhydride to yield a substituted, S-protected succinic acid, wherein the primary amino group of the intended first member adds to one of the carboxyl groups of the anhydride. See FIG. 5. This frees the remaining carboxyl group, in the form of a free carboxyl function to which one of the remaining tridentate members can be relatively easily attached. Following deprotection, the mercapto group can be attached to yet another tridentate member, as is shown in FIG. 5.

As with pyroglutamic acid, and other acid anhydrides, two isomeric tridentates are ultimately formed. As a result, the section of spacer moiety connecting each of the two members attached through the carboxyl groups varies by one bond. Ordinarily, this slight variation in spacer length does not affect the performance of the tridentate. In the unusual circumstance where it is desired to use only one particular isomer, the desired isomer can be separated out of the mixture at an early stage, following the initial addition reaction, using standard separation procedures.

The various section lengths of the spacer moiety can be easily controlled or varied using methods similar to those earlier set forth for varying the spacer length connecting two bifunctional conjugate members. For example, a series of diamine homologs is particularly useful in adding spacer length to an intended tridentate member where a primary amine is necessary for attachment to the starting spacer moiety. Adjustments in spacer section length are ordinarily made prior to attachment to the starting spacer moiety.

B. Carbobenzoxylysine As Starting Spacer Moiety

A good example of a starting spacer moiety requiring protection of one of two identical functional groups is lysine. The commercially available ω-carbobenzoxylysine (ω-CBZ-lysine) provides a good "preprotected" starting spacer moiety for the synthesis of a variety of tridentates. The carbobenzoxy protecting group is attached to the second amino function at the ω-position of the lysine molecule and is removed only after the α-amino function has been derivatized. It is often convenient, but not necessary, to attach the intended first member to the α-amino group of ω-CBZ-lysine.

Figure 6:
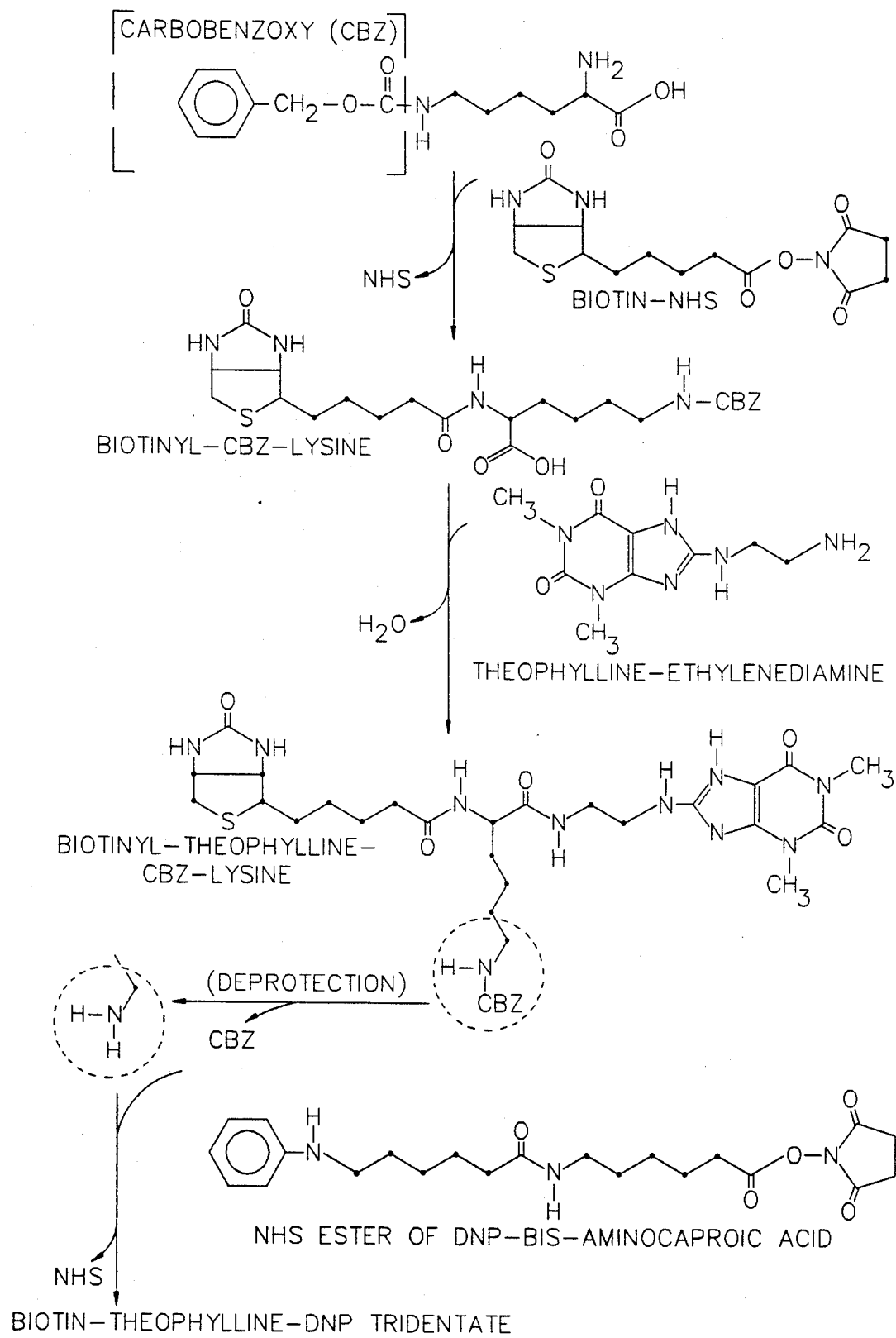
FIG. 6 schematically represents the synthesis of a biotin-theophylline-DNP tridentate using carbobenzoxylysine as the starting spacer moiety.

The preprotected ω-CBZ-lysine may be used as the starting spacer moiety in the synthesis of tridentates employing the steric hindrance embodiment of the present invention as well as in the synthesis of tridentates employing the targeted labeling embodiment. For example, a universal biotin-theophylline-DNP tridentate, useful in competitively modulated assays for theophylline such as the previously discussed NIIA shown in FIG. 1, may be conveniently synthesized from ω-CBZ-lysine. The synthesis of this tridentate is schematically shown in FIG. 6.

The first tridentate member, biotin, may be attached to the α-amino group of ω-CBZ-lysine (spacer) by utilizing the commercially available activated form of biotin, biotin-NHS. (Biotin-X-NHS may, for example, be used where a longer spacer is desired). The ω-CBZ-lysine is first dissolved in a bicarbonate solution and then heated to boiling to effect dissolution. Upon being cooled back to room temperature and then filtered, biotin-NHS (activated first member) is added to the solution, whereupon the activated carboxyl group of biotin readily condenses with the α-amino group of lysine, as is shown in FIG. 6. Solids of the derivatized biotinyl-CBZ-lysine (first member-spacer) may then be collected by standard filtration methods. It is ordinarily unnecessary to further purify the biotinyl-CBZ-lysine before proceeding with attachment of the second member.

The second tridentate member, theophylline is attached, in the form of a primary amine, to the activated α-carboxyl group of the derivatized lysine. The attachment of theophylline may take place either before or after conjugation of the protected ω-amino group. The desired primary amine derivative of theophylline may be prepared from 8-bromotheophylline as previously set forth as the first step in the synthesis of bifunctional conjugate I. The sections of the spacer moiety connecting theophylline to the other two tridentate members may be controlled through the selection of the particular diamine used to prepare the primary amine derivative of theophylline. Ethylenediamine may, for example, be used to prepare theophylline-ethylenediamine. The desired primary amine derivative of theophylline, thus prepared, is dissolved in anhydrous DMF in preparation for its conjugation to the starting spacer moiety.

The biotinyl-CBZ-lysine (first member-spacer) solids, obtained from the derivatization of the α-amino group of the lysine spacer, are dissolved in anhydrous DMF and heated to approximately 70° C. whereupon the α-carboxyl group of the lysine spacer is activated by the addition of CDI. After cooling back to room temperature, the predissolved selected primary amine derivative of theophylline (second member), e.g., theophylline-ethylenediamine, is added to the solution. The activated α-carboxyl group of the lysine spacer readily condenses with the primary amine derivative of theophylline, as is shown in FIG. 6, forming a precipitate containing the derivatized biotin-theophylline-CBZ-lysine (first member-second member-spacer) which may then be collected by standard filtration methods and dried. The biotin-theophylline-CBZ-lysine conjugate may be purified by subjecting the precipitate to separation chromatography on a silica gel column using a gradient chloroform:methanol mixture.

The carbobenzoxy protecting group must be removed from the ω-amino group of the twice derivatized lysine spacer before the ω-amino group can be conjugated to the third member. Removal of the carbobenzoxy protecting group can be effected in a number of ways. One convenient way is to dissolve the isolated biotin-theophylline-CBZ-lysine (first member-second member-spacer) in a commercially available 30% (wt. %, density 1.262) mixture of hydrobromic acid in acetic acid. The acid mixture is then diluted with deionized water and subsequently neutralized with solid sodium bicarbonate. The ω-amino group of the now deprotected biotin-theophylline-lysine conjugate (first member-second-member spacer) may be derivatized using an activated carboxyl group at the terminal end of the intended third member.

A terminal carboxyl group may be attached to the intended third member, DNP, by reacting Bis-aminocaproic acid with 2,4-dinitro-fluorobenzene (a DNP precursor also known as Sanger's reagent) to form DNP-Bis-aminocaproic acid. This reaction reaches completion at room temperature in about two hours. As is seen in FIG. 6, Bis-aminocaproic acid contributes 14 atoms to the common section of spacer moiety connecting DNP to the other tridentate members. The length of this section of the spacer can easily be controlled using an alternate ω-amino acid other than Bis-aminocaproic acid. For example, 5-aminopentanoic acid can be condensed with 6-aminocaproic acid to form a 13 atom spacer insert.

The DNP-Bis-aminocaproic acid (third member-spacer insert) may be isolated and purified by evaporating the reaction mixture to dryness, redissolving the residue in deionized water, acidifying the solution with hydrochloric acid, and then extracting the DNP-Bis-aminocaproic acid (third member-spacer insert) with ethyl acetate. The ethyl acetate may then be eliminated and the DNP-Bis-aminocaproic acid further purified using standard silica gel column chromatographic procedures.

CDI and NHS are used to activate the terminal carboxyl group of the DNP-Bis-aminocaproic acid (third member-spacer insert) by forming the reactive NHS ester of the acid. This reaction takes place relatively quickly in anhydrous chloroform. The chloroform solution is evaporated to near dryness and then brought back up to volume with anhydrous DMF, whereupon it is added to the previously set aside solution containing the deprotected biotin-theophylline-lysine (first member-second member-spacer). The condensation reaction between the exposed ω-amino group of the lysine spacer moiety and the activated carboxyl group of the DNP-Bis-aminocaproic acid (activated third member-spacer insert) occurs quite readily thus attaching the third member of the biotin-theophylline-DNP tridentate (first member-second member-third member).

Figure 8:
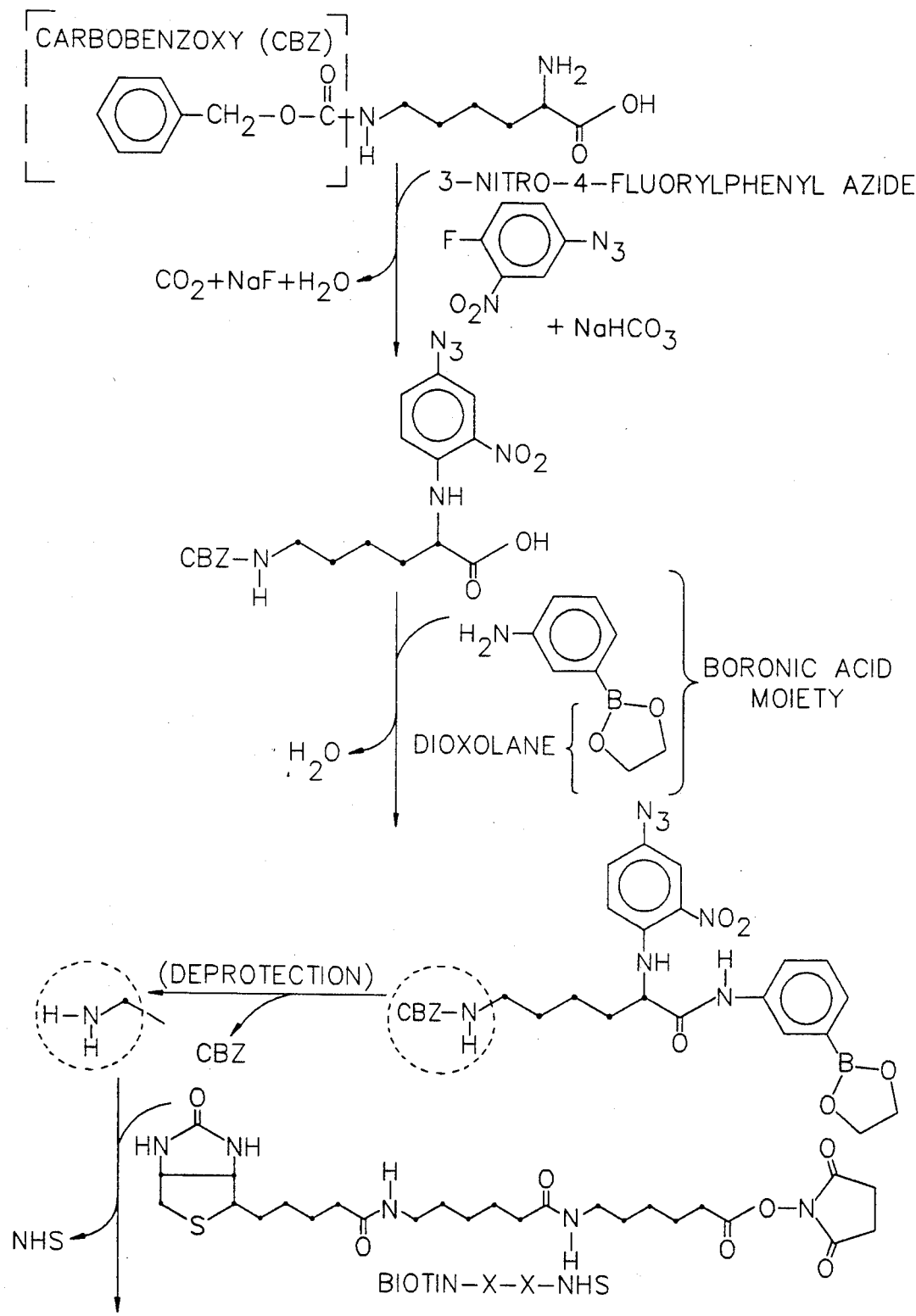
FIG. 8 schematically represents the synthesis of a phenylboronic acid-nitrophenylazido-biotin tridentate using carbobenzoxylysine as the starting spacer moiety.

The same commercially available preprotected ω-CBZ-lysine may also be used as the starting spacer moiety for a tridentate employing the targeted labeling embodiment of the present invention. The synthesis of a phenylboronic acid-nitrophenyl azido-biotin conjugate, for example, is shown in FIG. 8.

As with the synthesis of the biotin-theophylline-DNP tridentate, the carbobenzoxy protecting group is removed only after the α-amino function of the CBZ-lysine has been derivatized. The reactive azide member is first attached to the CBZ-lysine by reacting 3-nitro-4-fluorophenylazide with the α-amino group of CBZ-lysine as is shown in FIG. 8. The azide moiety readily attaches to the CBZ-lysine spacer, producing azide-CBZ-lysine (reactive member-spacer).

The α-carboxyl function of the derivatized CBZ-lysine is generally activated with CDI and NHS prior to further derivatization at the α-carboxyl position. A boronic acid moiety (guiding member) having a primary amine available for conjugation may then be attached to the activated α-carboxyl function of the derivatized azide-CBZ-lysine, through a standard condensation reaction. See FIG. 8.

The third tridentate member is attached to the twice-derivatized boronic acid-azide-CBZ-lysine (guiding member-reactive member-spacer) only after the carbobenzoxy protecting group is removed. This can again be accomplished by dissolving the boronic acid-azide- CBZ-lysine (guiding member-reactive member-spacer) in a commercially available 30% (wt. %, density 1.262) mixture of hydrobromic acid in acetic acid. This acid mixture may be diluted with deionized water and subsequently neutralized with sodium bicarbonate. The ω-amino group of the now deprotected boronic acid-azide-lysine conjugate (guiding member-reactive member-spacer) may be derivatized using an activated carboxyl group at the terminal end of the intended third member.

Where biotin is the intended third member, the commercially available biotin-NHS (5 atoms added to spacer) or biotin-X-NHS (12 atoms added to spacer) may be used. Alternatively, Bis-caproamidobiotin (biotin-X-X-NHS) may be conveniently used where 19 atoms are desired to be added to the spacer. All of these "preactivated" biotin derivatives readily condense with the ω-amino group of the lysine starting spacer moiety to yield the desired boronic acid-azide-biotin (guiding member-reactive member-intended label) tridentate conjugate. The tridentate conjugate shown in FIG. 9 results where biotin-X-X-NHS is employed in the final derivatization step.

C. Other Tridentates

Figure 10:
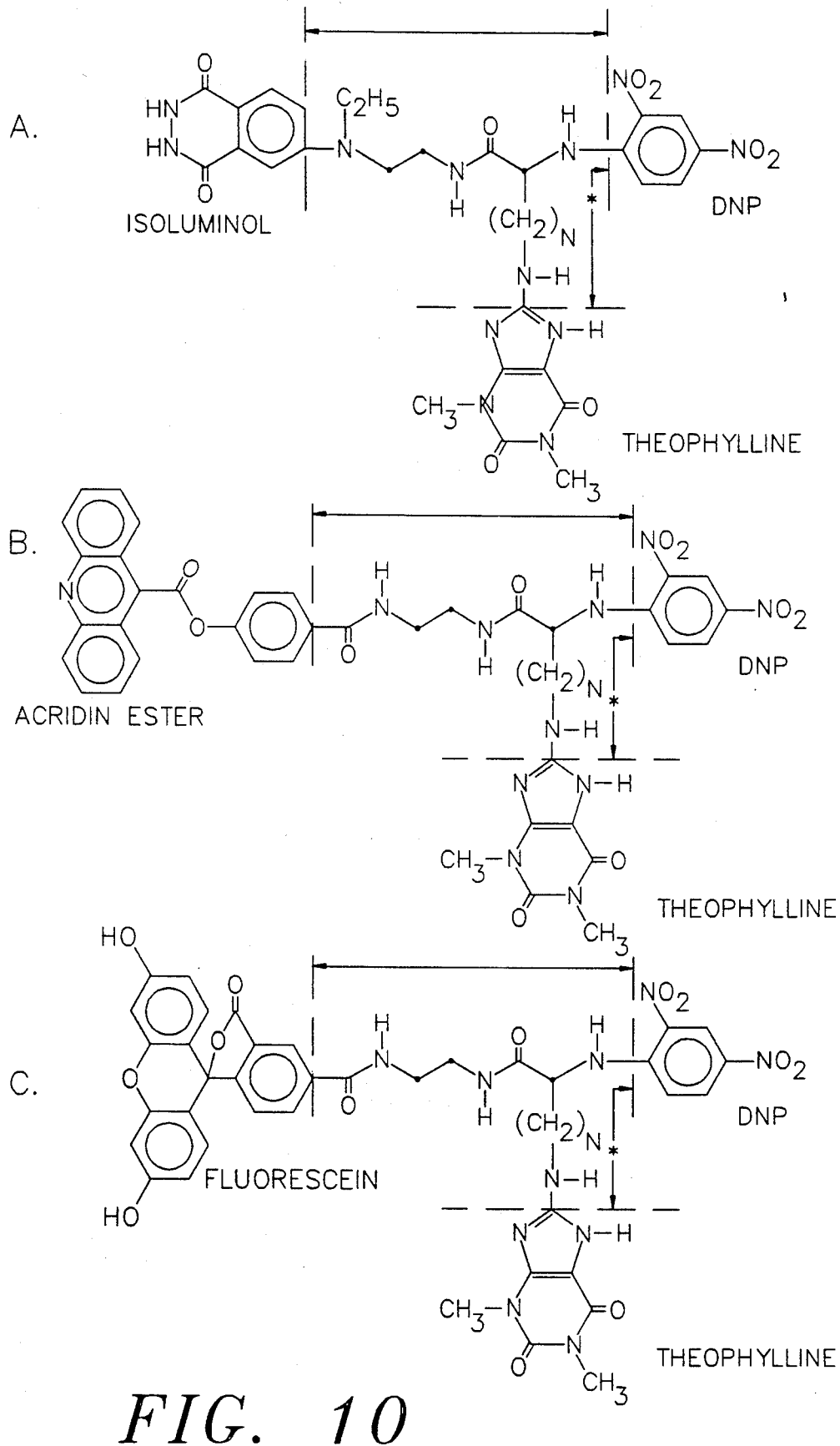
FIG. 10 illustrates the configuration of three different tridentates intended for use in an energy transfer assay using the steric hindrance embodiment of the present invention wherein one of the tridentate members is a proximity label.

Still other tridentates of the present invention can be synthesized using CBZ-lysine, cyclic acid anhydrides, or other suitable starting spacer moieties. For example, the tridentates shown in FIG. 10 may be readily synthesized for use in energy transfer assays employing the steric hindrance embodiment of the present invention wherein one of the first or third tridentate members is a proximity label. The different energy donor proximity labels may conveniently be attached as tridentate members. It will be apparent to those skilled in the art how to make these and other tridentate conjugates in light of the foregoing discussion.

EXAMPLE 1

Synthesis of Bifunctional Conjugate I

The synthesis of bifunctional conjugate I using hexanediamine (N=6) as the variable for insertion into the spacer is schematically shown in FIG. 2. The N=6 homolog of bifunctional conjugate I was produced in the following manner:

An excess of hexanediamine ($NH_2-(CH_2)_6-NH_2$) was refluxed with 8-bromotheophylline under a nitrogen atmosphere for a period of 24 hours. The end of the reflux reaction was determined by TLC analysis of the reaction mixture, using glass TLC plates coated with silica gel, and using an ultra-violet indicator.

The reaction mixture was then evaporated to a small volume under vacuum. The concentrated reaction mixture was mixed with a small quantity of silica gel and dried on a hot plate with the silica gel-sample mixture then being carefully loaded onto the top of a silica gel column using chloroform as the starting eluant. The column was eluted with solvent containing varying amounts of methanol in chloroform. When the gradient composition reached 20% methanol in chloroform, the column was eluted with a mixture containing 20% methanol, 4% ammonia, and 76% chloroform. The fractions containing the pure N-(8'-theophylline)-6-aminohexylamine were pooled and evaporated to dryness in a rotary evaporator. White-yellowish crystalline solids were used for the next reaction without further purification.

Equimolar quantities of the N-(8'-theophylline)-6-aminohexylamine crystalline solids were dissolved in anhydrous DMF, then mixed with the corresponding molar quantity of biotin-X-NHS and stirred overnight at room temperature. The desired products separated out of DMF as white, flocculent solids, and were collected on filter paper and purified to a single spot in a TLC test by column chromatography.

The chain length of the spacer moiety is controlled by the diamine ($NH_2-(CH_2)_N-NH_2$) selected for use in the synthesis of the bidentate. For example, where hexanediamine is selected for the first synthesis step, six carbon atoms are contributed to the spacer moiety chain length, as shown in FIG. 2. In this instance, the approximate length of the spacer moiety is 26.0 Å. The chain length obtained from the insertion of various diamines into the spacer of bifunctional conjugate I, using a procedure similar to that used to prepare the N=6 homolog, is shown in Table I.

TABLE I

| Length of Spacer Moiety in Bifunctional Conjugate I Homologs | | |
|---|---|---|
| Diamine | Total Number of Atoms in Spacer | Approximate Spacer Length (Å) |
| N = 2 | 16 | 21.0 |
| N = 3 | 17 | 22.2 |
| N = 4 | 18 | 23.5 |
| N = 5 | 19 | 24.8 |
| N = 6 | 20 | 26.0 |
| N = 7 | 21 | 27.3 |
| N = 8 | 22 | 28.5 |

EXAMPLE 2

Determination of Minimum Spacer Length

Minimum spacer length was determined by detecting the amount (rate) of signal generated by each of the conjugates identified in Table 1 in the presence of anti-theophylline antibody and avidin. The purpose of these measurements was simply to determine minimum spacer length for optimal binding at stoichiometric proportions of bifunctional conjugate, antibody, and avidin.

The reagents were prepared as follows: monoclonal antibody against theophylline was diluted 1:13.3 in ICS TM Diluent (Beckman Instruments, ICS TM Reagent). Avidin, purchased from Boehringer Mannheim, was dissolved in ICS diluent at a concentration of 0.13 mg/mL. Various dilutions of each of the bidentate conjugates listed in Table 1 were dissolved in 0.1M phosphate buffer, pH 5.5.

Nephelometric measurements were taken on an ICS TM nephelometer (Beckman Instruments) by placing 600 µL of ICS Buffer (Beckman Instruments, ICS TM Reagent) into an ICS TM vial (Beckman Instruments), and injecting 42 µL of antibody solution and 42 µL of avidin solution. After the injection transient subsided and the base-line was obtained, 42 µL of the bidentate conjugate were added and the instrument triggered to record the peak rate signal.

Figure 12:
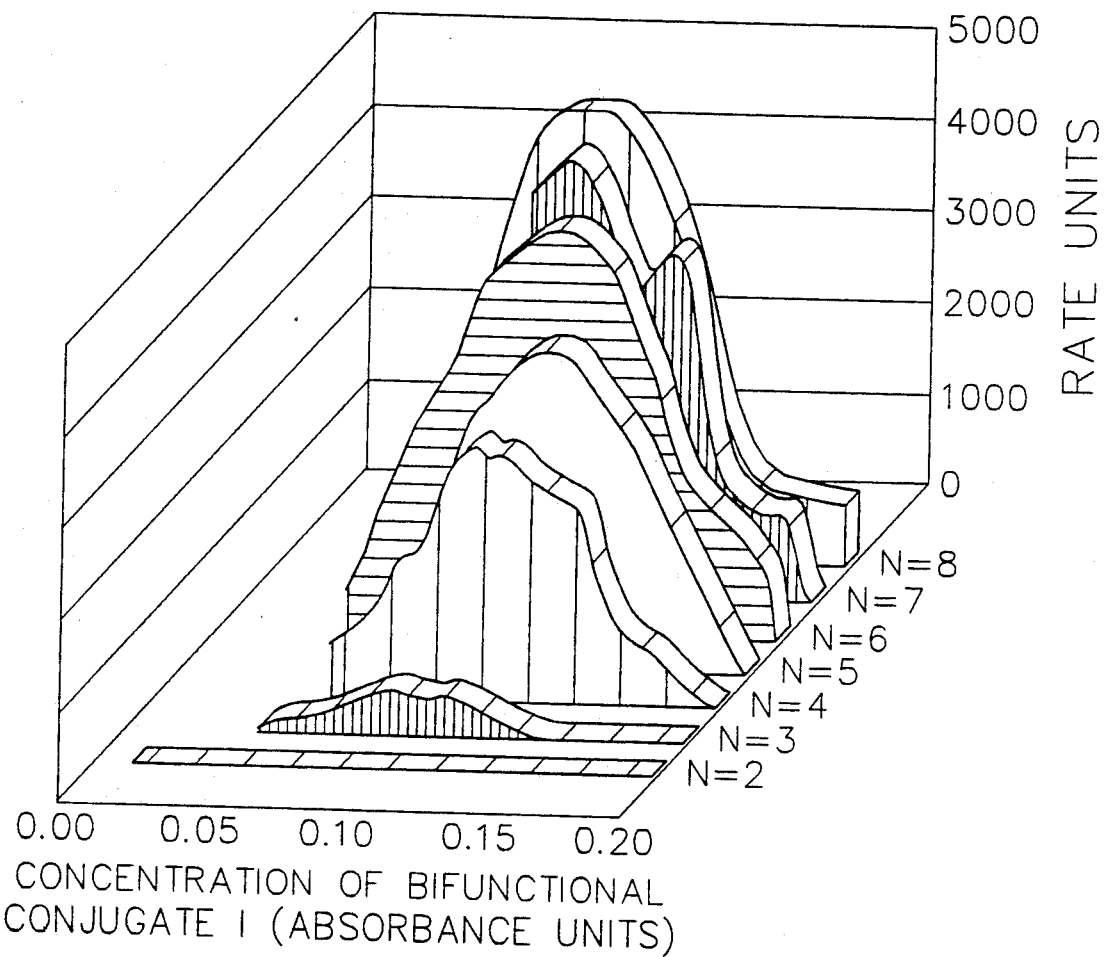
FIG. 12 demonstrates the effect of spacer length on the ability of the first and third members of a tridentate conjugate to simultaneously bind to their respective macromolecular specific binding partners in the absence of modulation.

The results for N=2 through N=8 are reported in FIG. 12. In FIG. 12, the units on the horizontal axis represent bidentate concentration based on absorbance at 295 nm. The units on the vertical axis are ICS TM rate units, obtained using the ICS TM Manual Mode Card M33 (Beckman Instruments). For high rate signals, above 2000 units, the ICS TM lower gain card was used and the results calculated for M33 gain.

As is seen in FIG. 12, the lowest homolog of bifunctional conjugate I (N=2), having 17 bonds (16 atoms)

between the theophylline ring carbon and the alicyclic ring carbon of biotin failed to yield measurable complex formation. The next higher homolog (bifunctional conjugate I, N=3) began to show measurable complexing. The higher homologs (N=4 through N=8) produced correspondingly higher signal until a plateau was reached at N=8. This study shows that a minimum spacer length of approximately 22.2 Å is required in order to produce signal where theophylline and biotin are employed as the first and third tridentate members. Optimally, the spacer length should be at least about 23.5 Å (bifunctional conjugate I, N=4), and more preferably about 26.0 to about 28.5 Å (bifunctional conjugate I, N=6 to N=8, or 20 to 22 atoms in the spacer).

The data of Example 2 and FIG. 12 shows that signal was generated with a minimum distance of about 22 Å between the members of bifunctional conjugate I; thus, if the distance between the members is less than about 22 Å, steric hindrance effects between these members prevents the generation of signal. The data further demonstrates that at a separation distance of about 26 Å to about 28 Å, signal is consistently achieved for bifunction conjugate I. I.e. there are not steric hindrance effects between these conjugate members. Therefore, to ensure that signal is generated, a minimum separation distance of about 28 Å between the conjugate members is preferred.

EXAMPLE 3

Synthesis of Bifunctional Conjugate II

A second bifunctional conjugate was prepared to confirm the results obtained for bifunctional conjugate I and to demonstrate an alternate synthesis method. The synthesis of bifunctional conjugate II using hexanediamine as the variable for insertion into the spacer is schematically shown in FIG. 5. The N=6 homolog of bifunctional conjugate II was produced in the following manner:

Theophylline-8-butyric acid was dissolved in anhydrous DMF, then heated to about 70° C. with the subsequent addition of an equimolar quantity of CDI. The reaction temperature was maintained at about 70° C. for approximately 15 minutes, then allowed to cool to room temperature. An equimolar quantity of NHS was then added to the cooled reaction mixture and stirred overnight at room temperature. An approximate three to six molar excess of hexanediamine ($H_2N$—$(CH_2)_6$—$NH_2$) was then added to the reaction mixture. The completion of reaction was determined by TLC analysis of the reaction mixture, using TLC plates coated with silica gel and an ultraviolet indicator.

The reaction mixture was then evaporated to a small volume under vacuum. The concentrated reaction mixture was mixed with a small quantity of silica gel and dried on a hot plate with the silica gel-sample mixture then being carefully loaded onto the top of a silica gel column using chloroform as the starting eluant. The column was eluted with solvent containing varying amounts of methanol in chloroform. When the gradient composition reached 20% methanol in chloroform, the column was eluted with a mixture containing 20% methanol, 4% ammonia, and 76% chloroform. The fractions containing the pure 6-(8'-theophylline butyric carboxamido)-hexylamine were pooled and evaporated to dryness in a rotary evaporator. White-yellowish crystalline solids were used for the next reaction without further purification.

An equimolar quantity of the 6-(8'-theophylline butyric carboxamido)-hexylamine was dissolved in anhydrous DMF, then mixed with the corresponding molar quantity of biotin-NHS and left stirred overnight at room temperature. The desired products separated out of DMF as white, flocculent solids, and were collected on a filter paper and purified to a single spot in a TLC test by preparative thin layer chromatography.

The N=5 homolog of bifunctional conjugate II was prepared using an identical procedure with the exception that pentanediamine was used in place of hexanediamine. The spacer lengths for the two homologs are set forth in Table II.

TABLE II

| Length of Spacer Moiety in Bidentate Conjugate II Homologs | | |
|---|---|---|
| Diamine | Total Number of Atoms in Space | Approximate Spacer Length (Å) |
| N = 5 | 16 | 21.0 |
| N = 6 | 18 | 22.2 |

The N=2 homolog of bifunctional conjugate I is equivalent to the N=5 homolog of bifunctional conjugate II (21.0 Å). The N=3 and N=6 homologs of bifunctional conjugates I and II, respectively, are also equivalent (22.2 Å). The N=5 homolog of the second series, like the N=2 homolog of the first series failed to yield measurable complexing. Comparable signals were obtained, however for the N=6 homolog of bifunctional conjugate II and the N=3 homolog of bifunctional conjugate I. This confirms that at least a 22.2 Å spacer moiety is required to achieve simultaneous binding of the first and third tridentate members to their specific binding partners where theophylline and biotin or similar haptens and/or small molecules are chosen as the first and third tridentate members. Further, because no signal was generated when the spacer length was about 21.0 Å, the distance between the first and third members is preferably less than this distance, i.e., less than about 20 Å.

EXAMPLE 4

Synthesis of biotin-theophylline-DNP Tridentate

A universal biotin-theophylline-DNP tridentate conjugate, for use in competitively modulated immunoassays for theophylline, was synthesized using CBZ-lysine as the starting spacer moiety. The optimal minimum spacer length data from the biotin-theophylline bifunctional conjugate I homolog study was used as the starting point for designing the biotin-theophylline-DNP tridentate. Specifically, an optimal minimum spacer length of about 26.0 to about 28.5 Å, or 20 to 22 atoms in the spacer, was established for simultaneous binding of the biotin and theophylline members of a bifunctional conjugate. (See Example 2.) A 10 to 20% increase, or about 22 to 26 atoms, was thus believed to be optimal for obtaining simultaneous binding of the biotin and DNP (first and third) members of the tridentate in the absence of modulation. Biotin was selected to be the modulated member, with a much shorter spacer length, on the order of 12 atoms, being chosen for the section of the spacer moiety connecting theophylline (modulating member) with biotin.

Attachment of First Tridentate Member

The starting spacer group, ω-carbobenzoxy-lysine (CBZ-lysine), was added to a 10% sodium bicarbonate solution which was heated to boiling to effect dissolution and then cooled back to room temperature. The cooled solution was then filtered through fluted filter paper. An equimolar quantity of biotin-NHS, containing the intended first member biotin, was added to the solution and stirred at room temperature for about 24 hours. White solids of biotinyl-CBZ-lysine formed during the course of the reaction and were collected by standard filtration methods. This crude preparation of biotinyl-CBZ-lysine was used in the further preparation of the tridentate without being subjected to additional purification steps.

Attachment of Second Tridentate Member

The biotinyl-CBZ-lysine was dissolved in anhydrous DMF and the mixture heated to approximately 70° C. whereupon the carboxyl group of the lysine moiety was activated by the addition of CDI. The activation process was allowed to proceed for about 15 minutes before the solution was cooled back to room temperature. The cooled mixture was then stirred at room temperature for an additional 30 minutes. An equimolar quantity of theophylline-ethylenediamine was first dissolved in DMF and then added to the cooled mixture, which was left stirring overnight at room temperature. A white precipitate containing biotin-theophylline-CBZ-lysine formed overnight and was collected by standard filtration methods and dried.

The precipitate contained a relatively minor unidentified contaminant which was separated out on a silica gel column using a gradient chloroform:methanol mixture. The precipitate was mixed with a small quantity silica gel and then carefully loaded onto the top of a silica gel column using chloroform as the starting eluant. The column was eluted with solvent containing varying amounts of methanol in chloroform, until the gradient composition reached 20% methanol in chloroform. The first compound to be eluted from the column was the biotin-theophylline-CBZ-lysine which was collected and evaporated to dryness, yielding a white crystalline powder. Ultraviolet absorption and TLC analysis of the white crystalline powder confirmed that the product contained both the biotin and theophylline moieties.

Attachment of Third Tridentate Member

In order to attach the third tridentate member, three steps were required: (1) the ω-amino group at the third member position of the lysine moiety had to be deprotected; i.e., by the removal of the CBZ group; (2) a carboxyl group had to be attached to the end of the intended third member; and, (3) the attached carboxyl group had to be activated in order to react with the free amino group at the third member position of the lysine moiety.

The carbobenzoxy protecting group was removed from the ω-amino group of the lysine spacer by dissolving the white crystalline powder in an excess of commercially available 30% (wt. %, density 1.262) hydrobromic acid in acetic acid. The acid mixture was diluted to approximately 50 times its original volume with deionized water and then neutralized with solid sodium bicarbonate until the pH of the solution was brought up to about 8-9. The neutralized solution was then set aside while the intended third member was prepared for attachment.

A terminal carboxyl group was attached to the intended third member (DNP) of the tridentate by reacting Bis-aminocaproic acid with 2,4-dinitrofluorobenzene (Sanger's reagent). Specifically, an excess of 2,4-dinitrofluorobenzene was added to Bis-aminocaproic acid which had previously been dissolved in a 1M solution of sodium bicarbonate, and allowed to react at room temperature for about two hours. The reaction mixture was evaporated to dryness in a rotary evaporator under reduced pressure. The residue was then redissolved in deionized water and acidified to about pH 1 with 28% (wt. %) hydrochloric acid. Yellow precipitate containing DNP-Bis-aminocaproic acid formed and was extracted with ethyl acetate, which was then eliminated by using a rotary evaporator, leaving a yellow solid. The solid was further purified using a standard silica gel column chromatographic procedure similar to that outlined above for the purification of biotin-theophylline-CBZ-lysine.

Dicyclohexylcarbodiimide (DCCI) and NHS were used to activate the terminal carboxyl group of the DNP-Bis-aminocaproic acid by forming the reactive NHS ester of the acid. The purified DNP-Bis-aminocaproic acid was first dissolved in anhydrous chloroform, to which DCCI and NHS were subsequently added. The NHS ester of DNP-Bis-aminocaproic acid quickly formed within about 60 minutes. TLC analysis indicated the ester to be pure, but the ester proved difficult to crystallize, nonetheless. Consequently, the solution was evaporated to near dryness and then brought back up to volume with anhydrous DMF.

Figure 7:
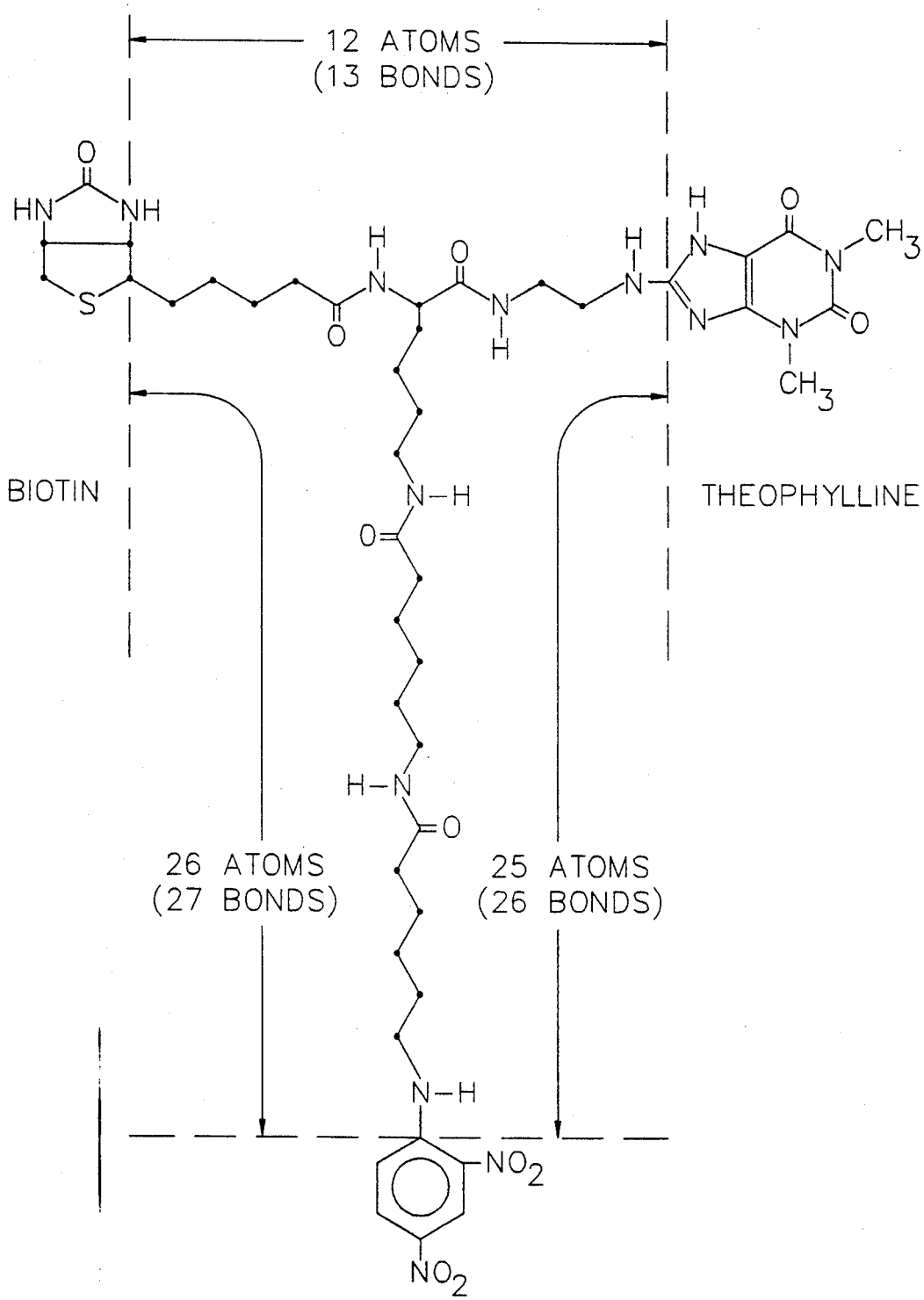
FIG. 7 illustrates the configuration of a biotin-theophylline-DNP tridentate intended for use in the steric hindrance embodiment of the invention.

The DMF solution containing the activated NHS ester of DNP-Bis-aminocaproic acid was then added to the previously set aside solution containing the deprotected theophylline-biotin-lysine. The condensation reaction between the exposed ω-amino group of the lysine spacer moiety and the activated carboxyl group of the DNP-Bis-aminocaproic acid occurred quite readily at room temperature, thus attaching the third member to the tridentate. The structure of the completed tridentate is shown in FIG. 7.

EXAMPLE 5

Bidentate Conjugate I in NIIA for Theophylline-amine

A NIIA type of assay for theophylline-amine was successfully run using the biotin-theophylline-DNP tridentate from Example 4. Free theophylline-amine, from standardized solutions, competed with the second tridentate member for a limited quantity of antitheophylline antibody. Increasing concentrations of theophylline-amine resulted in decreased modulation and increased nephelometric signal. The same tridentate and assay conditions can be used to test for theoplylline.

The reagents were prepared as follows: Monoclonal antibody against theophylline was diluted 1:20 in ICS TM Diluent (Beckman Instruments, ICS TM Reagent). Rabbit anti-DNP antiserum, purchased from Miles Laboratories, was dialyzed in ICS Diluent prior to use. Avidin, purchased from Boehringer Mannheim, was dissolved in ICS diluent at a concentration of 0.25 mg/mL. The tridentate conjugate was dissolved in ICS Diluent at a concentration of $2.06 \times 10^{-8}$ moles/mL. Theophylline-amine was diluted in ICS diluent to a concentration of $2.8 \times 10^{-8}$ moles/mL. Similar solutions were made up to final concentrations of $1.4 \times 10^{-8}$ and $0.56 \times 10^{-8}$ moles/mL, respectively.

A 138 μL aliquot of monoclonal anti-theophylline antibody solution was deposited in a test tube, followed by the addition of 18.4 μL of theophylline-amine at $2.8 \times 10^{-8}$ moles/mL. The resulting mixture was then stirred for two minutes at room temperature. A 30 μL aliquot of the tridentate conjugate solution was then added to the test tube, which was mixed and then left standing for about two minutes.

Nephelometric measurements were taken on an ICS TM nephelometer (Beckman Instruments) by placing 600 μL of ICS Buffer (Beckman Instruments, ICS TM Reagent) into an ICS TM vial (Beckman Instruments), and injecting 31 μL of the above mixture, and 50 μL of anti-DNP antiserum solution. An instrument gain setting of Manual Mode M33 was used. After the injection transient subsided and the baseline was obtained, 10 μL of the avidin solution was added and the instrument triggered to record the peak rate signal.

The same procedure was then repeated using 18.4 μL of the theophylline-amine solutions at $1.4 \times 10^{-8}$ and $0.56 \times 10^{-8}$ moles/L and 18.4 μL of ICS Diluent (zero dose test). The results are set forth in Table III.

TABLE III

| Theophylline-amine Concentration (moles/mL) | Rate Units |
| --- | --- |
| 0 | 158 |
| 0 | 171 |
| 0 | 165 |
| $0.56 \times 10^{-8}$ | 240 |
| $0.56 \times 10^{-8}$ | 265 |
| $0.56 \times 10^{-8}$ | 218 |
| $1.40 \times 10^{-8}$ | 365 |
| $1.40 \times 10^{-8}$ | 389 |
| $1.40 \times 10^{-8}$ | 361 |
| $2.80 \times 10^{-8}$ | 648 |
| $2.80 \times 10^{-8}$ | 638 |
| $2.80 \times 10^{-8}$ | 610 |

EXAMPLE 6

Enzyme Channeling Using Universal Tridentate

The same biotin-theophylline-DNP tridentate can be used to perform a competitively modulated enzyme channeling assay. For example, a first enzyme, such as hexokinase, is attached to either avidin or anti-DNP antibody. A second enzyme, such as G6PDH, is attached to the other specific binding partner. Free theophylline or theoplylline-amine, contributed by a test sample or a calibration standard, modulates enzyme channeling by diverting anti-theophylline antibody away from the second (modulating) member of the tridentate.

Preparation of HK-Avidin Conjugate

Hexokinase is thiolated by suspending the HK enzyme in 0.1M phosphate buffer, pH 7.5, containing 20% (v/v) DMF, and incubating the suspension with S-acetylmercaptosuccinic anhydride. After allowing the reaction to reach completion, the thiol groups of the hexokinase are deblocked by treating the mixture with 1.0M hydroxylamine, pH 7.5. The thiolated hexokinase can be isolated by either passing the mixture through a Sephadex ® G-50 (bead-formed, cross-linked dextran, Pharmacia, Uppsala, Sweden) column or by standard dialysis methods.

Avidin is also suspended in a 0.1M phosphate buffer solution, pH 7.5, containing 20% (v/v) DMF, and then treated with meta-maleiimidobenzoyl-N-hydroxysuccinimide (MBS-NHS). The reaction mixture can then be passed through a Sephadex ® G-50 column to isolate the MBS-labeled avidin.

Equimolar quantities of the thiolated hexokinase and MBS-labeled avidin are then incubated to obtain the HK-avidin conjugate.

Preparation of G6PDH-Anti-DNP Antibody

The G6PDH-labeled anti-DNP antibody is prepared in much the same manner as the avidin-HK conjugate. The enzyme is first thiolated by suspending the G6PDH in 0.1M phosphate buffer, pH 7.5, containing 20% (v/v) DMF, and incubating the suspension with S-acetyl-mercaptosuccinic anhydride. After allowing the reaction to reach completion, the thiol groups of the G6PDH are deblocked by treating the mixture with 1.0M hydroxylamine, pH 7.5. The thiolated G6PDH can be isolated by either passing the mixture through a Sephadex ® G-50 column or by standard dialysis methods.

Anti-DNP antibody is also suspended in a 0.1M phosphate buffer solution, pH 7.5, containing 20% (v/v) DMF, and then treated with MBS-NHS. The reaction mixture can then be passed through a Sephadex ® G-50 column to isolate the MBS-labeled anti-DNP antibody.

Equimolar quantities of the thiolated G6PDH and MBS-labeled anti-DNP antibody are then incubated to obtain the G6PDH-anti-DNP antibody conjugate.

Determination of Optimum Reagent Concentrations for Enzyme Channeling

It is ordinarily desirable to determine the optimum reagent concentrations for the production of signal. This is the point at which: (1) maximum signal is obtained, in the absence of modulation; with, (2) minimum use of expensive reagents.

The following reagents are used:

Incubation buffer: 50 mM Bicin, pH 8.4, 100 mM KCl, 0.2% bovine serum albumin (BSA), 0.05% sodium azide.

Tridentate solution: tridentate conjugate dissolved in incubation buffer to a concentration equivalent to about 1 μg/mL theophylline.

Proximity label solution: equimolar quantities of HK-avidin and G6PDH-anti-DNP antibody suspended in incubation buffer. Various dilutions are prepared.

Antibody solution: anti-theophylline antibody suspended in incubation buffer. Various dilutions are prepared.

Substrate mixture: 50 mM Bicin, pH 8.4, 100 mM KCl, 6 mM $MgCl_2$, 3 mM ATP, 3 mM NAD+, 40 mM glucose, and 40% glycerol.

Initially, 100 μL of the tridentate solution and 100 μL of the proximity label solution are introduced into 800 μL of the substrate mixture. The rate of NADH production is a measure of the amount of glucose-6-phosphate, generated by the HK, which has been acted upon by the G6PDH before escaping into bulk solution; i.e., the rate of enzyme channeling. This reaction can be measured using a suitable fluorometer with 450 nm detection wavelength and 340 nm excitation wavelength settings. The measurements are repeated using increasing dilutions of the proximity label solution until the rate of NADH production begins to decrease. This establishes the minimum concentration of the proximity label solution required to generate maximum signal.

Once the minimum concentration of the proximity label solution is set, the optimum amount of antitheophylline antibody required to produce maximum steric hindrance is determined. To make this determination, 100 μL of tridentate solution are mixed with 100 μL of antibody solution and incubated for about 5 to 15 minutes. (The steady state equilibrium of the antigen:antibody reaction will establish very quickly, in contrast to systems wherein either the antigen or antibody is bound to a solid surface.) A 100 μL quantity of the optimized proximity label solution is then added and the entire reaction mixture incubated an additional 5 to 15 minutes. A 700 μL aliquot of the substrate solution is finally added and the rate of NADH production monitored using the fluorometer described above.

The assay is repeated with increasing concentrations (decreasing dilutions) of antibody solution until the rate of NADH production reaches a minimum point, whereupon the addition of increasing concentrations of antibody solution fails to further lower the rate. This is the minimum concentration of antibody solution required to generate maximum steric hindrance.

Assay for Analyte

A 100 μL aliquot of a patient's test sample is initially combined with a 100 μL aliquot of the tridentate solution. This combined solution is then incubated with 100 μL of the optimized antibody solution for a period of approximately 5 to 15 minutes. A 100 μL aliquot of the optimized proximity label solution is then added to the incubated mixture, and the combined solution further incubated for an additional 5 to 15 minutes. At this point, 600 μL of the substrate solution is added and the rate of NADH formation monitored using a suitable fluorometer.

The same procedure is then repeated for various dilutions of a theophylline or theophylline-amine standard, from which a standard curve can be obtained. The concentration of theophylline or theophylline-amine in the sample can be interpolated from the standard curve.

EXAMPLE 7

Energy Transfer Using Universal Tridentate

The same biotin-theophylline-DNP tridentate can also be used to perform a competitively modulated energy transfer assay. For example, an energy donor, such as the chemiluminescent molecule isoluminol, is attached to either avidin or anti-DNP antibody. An energy acceptor, such as fluorescein isothiocyanate, is attached to the other specific binding partner. Free theophylline or theophylline-amine, contributed by a test sample or calibration standard, modulates energy transfer by diverting anti-theophylline antibody away from the second (modulating) member of the tridentate.

Preparation of Isoluminol-Avidin Conjugate

An excess of an isothiocyanate derivative of aminobutylethylamino-isoluminol is dissolved in DMF. An avidin solution is then made by suspending avidin in a 0.1M sodium carbonate/sodium bicarbonate buffer at pH 9.5. The isoluminol-containing DMF solution is then added to the avidin solution and incubated at about 4° C. for about 12 hours. The excess isoluminol label can then be removed by extensive dialysis, followed by gel filtration using a Sephadex ® G-50 column.

Preparation of Fluorescein-Anti-DNP Antibody Conjugate

Fluorescein-labeled antibody can be prepared in a similar manner. An excess of fluorescein isothiocyanate is dissolved in p-dioxane. An antibody solution is then made by suspending rabbit anti-DNP antibody in a 0.1M sodium carbonate/sodium bicarbonate buffer at pH 9.5. The fluorescein-containing p-dioxane solution is then added to the antibody solution and incubated at about 4° C. for about 12 hours. The excess fluorescein label can then be removed by extensive dialysis followed by gel filtration through a Sephadex ® G-50 column.

Determination of Optimum Reagent Concentrations for Energy Transfer

The following reagents are used:

Incubation buffer: 50 mM phosphate buffer, pH 7.4.

Tridentate solution: tridentate conjugate dissolved in incubation buffer to a concentration equivalent to about 1 μg/mL theophylline.

Proximity label solution: equimolar quantities of isoluminol-avidin and fluorescein-anti-DNP antibody suspended in incubation buffer. Various dilutions are prepared.

Antibody solution: anti-theophylline antibody suspended in incubation buffer. Various dilutions are prepared.

Chemiluminescent triggering reagent: 5 μM microperoxidase (Sigma Chemicals) in 100 mM barbitone buffer, pH 9, 0.01% BSA, and 0.175M $H_2O_2$.

The maximum attainable chemiluminescence energy transfer at the given concentration of tridentate conjugate is first assessed.

Initially, 100 μL of the tridentate solution and 100 μL of the undiluted proximity label solution are incubated at room temperature for about 5 to 15 minutes. An aliquot of this mixture is then introduced into a luminometer having two band pass filters of 460 nm (fluorescein excitation wavelength) and 525 nm (fluorescein emission wavelength) in front of two photomultipliers. An adequate amount of chemiluminescent triggering reagent is then added to induce light emission by the isoluminol molecules present. The isoluminol molecules emit light at about 460 nm. Where the isoluminol is in close proximity with the fluorescein label, fluorescein will absorb the emitted light at 460 nm with the concommitant emission of fluorescent light energy at 525 nm. The ratio of light levels, 525 nm/460 nm increases with increasing energy transfer. These measurements are repeated using increasing dilutions of proximity label solution until the ratio of light levels begins to decrease. This establishes the minimum concentration of proximity label solution required to generate maximum signal.

Once the minimum concentration of the proximity label solution is established, the optimum amount of anti-theophylline antibody required to produce maximum steric hindrance is determined. To make this determination, anti-theophylline antibody is added to the incubation mixture prior to addition of the chemiluminescent triggering reagent. Increasing amounts of anti-theophylline antibody are added in subsequent determinations until a point is reached whereupon the addition of increasing concentrations of antibody solution fails to further lower the measurable energy transfer. This is the minimum concentration of antibody solution required to generate maximum steric hindrance.

Assay for Analyte

A 100 μL aliquot of a patient's test sample is initially incubated with a 100 μL aliquot of the optimized antibody solution. 100 μL aliquots of the tridentate solution and proximity label solution are then added and the combined solution further incubated for an additional 5 to 15 minutes. An aliquot of this combined solution is then introduced into a luminometer and an adequate amount of chemiluminescent triggering reagent added prior to signal being measured.

The same procedure is then repeated for various dilutions of a theophylline or theophylline-amine standard, from which a standard curve can be obtained. The concentration of theophylline or theophylline-amine in the sample can be interpolated from the standard curve.

EXAMPLE 7

Energy Transfer Where One of Tridentate Members is a Proximity Label

The same general procedure set forth in Example 6 may be followed where a tridentate having a proximity label as one of the tridentate members is employed.

For example, the tridentate shown in FIG. 10A may be employed. In this instance, the proximity label solution contains only the fluorescein-anti-DNP antibody. In all other respects, the same optimization and assay procedures set forth in Example 6 are followed.

EXAMPLE 8

Energy Transfer Where One of Tridentate Members is a Solid Support

The same general procedure set forth in Example 6 may also be followed where a tridentate having, as one of its members, a macromolecule conjugated to a plurality of proximity labels is employed. The macromolecule may be a solid support as shown in FIG. 11.

Where the tridentate shown in FIG. 11 is employed, the proximity label solution again contains only the fluorescein-anti-DNP antibody. In all other respects, the same optimization and assay procedures set forth in Example 6 are followed, with the exception that incubation times may have to be extended to account for the slower kinetics of a system utilizing a solid support.

EXAMPLE 9

Attachment of Biotin Label to Glycosylated Protein

Figure 9:
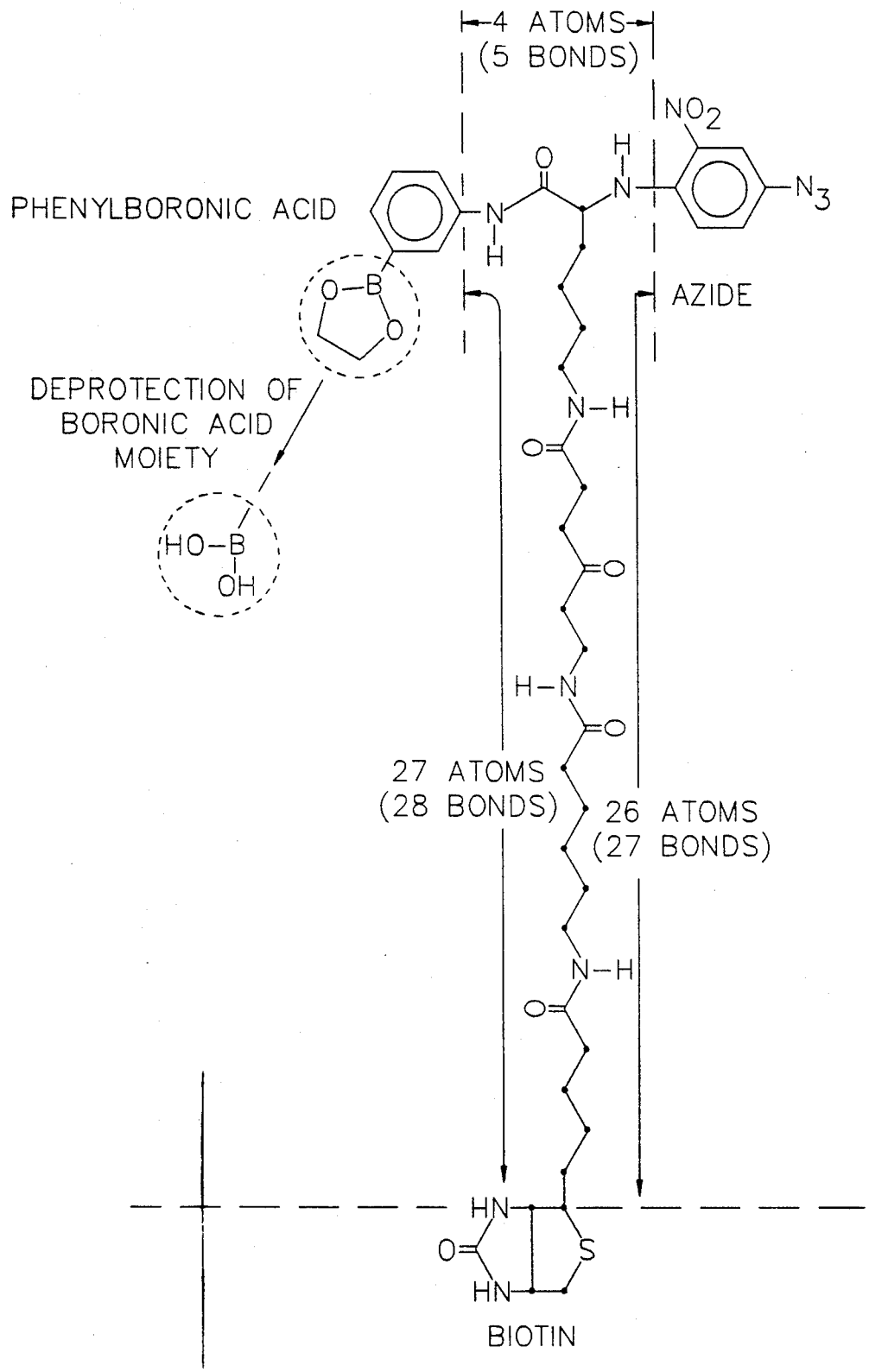
FIG. 9 illustrates the configuration of a phenylboronic acid-nitrophenylazido-biotin tridentate intended for use in the targeted labeling embodiment of the invention.

The boronic acid-azide-biotin tridentate shown in FIG. 9 may be used to attach a biotin label to a glycosylated protein at a designated site on the protein; i.e., at the sugar moiety. This procedure is particularly useful in biotinylating an antibody, enzyme, or antigen.

Targeted Binding of Guiding Member

The following reagents are used:

Glycosylated protein solution: any glycosylated protein solution, such as antibody solutions or ascites fluid, antigen solutions, and enzyme preparations, may be used. Many of these solutions are commercially available.

Buffer solution: 50 mM N-methylmorpholinium chloride, pH 7.2, 100 mM magnesium chloride.

Tridentate solution: The tridentate shown in FIG. 9 is dissolved in 10% (w/v) NaOH to deprotect the boronic acid moiety (guiding member) of the tridentate.

The glycosylated protein solution is dialyzed in the buffer solution and set aside. The tridentate solution is then diluted with the same buffer solution. An aliquot of the diluted tridentate solution, representing about a 10 to 100-fold molar excess of the tridentate relative to the total glycosylated protein in the glycosylated protein solution, is then removed. This aliquot is added to the dialyzed glycosylated protein solution, and the entire mixture is incubated at room temperature for about 2 hours in the dark.

Following incubation, the reaction mixture may be chromatographed in the dark on a Sephadex® G-50 column, with the protein fraction being isolated. The protein fraction will contain the boronate complex (bound guiding member).

Attachment of Reactive Member

The isolated product may then be irradiated with a suitable ultraviolet light source, such as a Mazda 125 W MB/V pearl glass lamp. The irradiation takes place at 0° C. from a distance of about 5 to about 20 cm from the illuminator. In order to insure complete conversion of the azide to nitrene, the irradiation may be continued for several hours. Photocoupling of the tridentate to the glycosylated protein takes place almost immediately upon conversion of the azide residue to nitrene. Following the photocoupling reaction, the reaction mixture can be dialyzed in almost any standard buffer solution, using standard dialysis techniques, to eliminate any photochemically uncoupled tridentate.

Still other types of tridentate conjugates and methods of use thereof are contemplated as being within the scope of this invention and will be apparent to those skilled in the art. As this invention may be embodied in several forms, without departing from the essential spirit thereof, the invention is intended to be defined by the appended claims as opposed to the foregoing description.

What is claimed is:

1. A trifunctional conjugate having a first member, a second member and a third member, each member being attached to an organic spacer moiety, wherein:
   (a) the first member is a reactive member capable of binding to at least one macromolecule, said macromolecule having at least one binding site for a ligand, said ligand being distinct from the first member, the second member and the third member,
   (b) the second member comprises at least one substituted boronic acid group capable of binding to said macromolecule having at least one binding site for a ligand, said ligand being distinct from the first member, the second member and the third member, said substituted bormic acid group not being capable of binding to ligand binding sites on said macromolecule;
   (c) the third member is a label; and
   (d) the spacer moiety is selected such that the binding of the second member to a macromolecule does not prevent binding of the reactive member to the same macromolecule.

2. The trifunctional conjugate of claim 1 wherein said reactive member is a moiety capable of forming a covalent bond with another moiety.

3. The trifunctional conjugate of claim 1 wherein said reactive member is a small molecule ligand.

4. The trifunctional conjugate of claim 1 wherein said second member is a phenyl boronic acid residue.

5. The trifunctional conjugate of claim 1 wherein said second member is capable of forming a covalent bond with another moiety.

6. The trifunctional conjugate of claim 1 wherein said reactive member is an azide residue.

7. The trifunctional conjugate of claim 5 wherein said reactive member is a moiety capable of forming a covalent bond with another moiety.

8. The trifunctional conjugate of claim 7 wherein said second member is a phenyl boronic residue and said reactive member is an azide residue.

9. The trifunctional conjugate of claim 8 wherein said label is biotin.

10. The trifunctional conjugate of claim 5 wherein said reactive member is a small molecule ligand.

11. The trifunctional conjugate of claim 10 wherein said reactive member is an azide residue.

12. The trifunctional conjugate of claim 1 wherein said reactive member and said second member are each capable of binding to at least one macromolecule which contains a carbohydrate moiety and said reactive member is capable of binding to said carbohydrate moiety.

13. The trifunctional conjugate of claim 1 wherein said organic spacer moiety is selected from the group consisting of cysteine, lysine, glutamic acid, pyroglutamic acid, S-acetylmercaptosuccinic anhydride, and ω-carbobenzoxylysine.

14. The preparation of claim 1 wherein said second member is a phenyl boronic acid residue and said reactive member is an azide residue.

15. The preparation of claim 1 wherein said label is biotin.

16. The trifunctional conjugate of claim 1 wherein two of the members are small molecules and the other member is selected from the group consisting of
  (i) small molecules,
  (ii) small molecule ligands, and
  (iii) macromolecules.

17. The trifunctional conjugate of claim 16 wherein said two members are each capable of binding to the same macromolecule.

18. The trifunctional conjugate of claim 16 wherein at least one of said two members is a moiety capable of forming a covalent bond with another moiety.

19. A preparation comprising at least two trifunctional conjugate molecules of claim 1 wherein the three members of the conjugate are separated from each other by distances controlled to within about one bond length, the controlled distances being substantially uniform for all molecules of the preparation.

20. The trifunctional conjugate of claim 1 wherein said label is biotin.

21. A preparation comprising at least two trifunctional conjugate molecules, each trifunctional molecule having three members, a first member, a second member and a third member, each member being attached together through an organic spacer moiety such that the three members are separated each from the other by distances controlled to within about one bond length, the controlled distances being substantially uniform for all molecules of the preparation, wherein at least two of the members are small molecules capable of binding with at least one small molecule binding partner and one of the members is a modulating member, wherein at least two of the members are separated from each other by at least about 28 Å, and the modulating member is separated from two of the members by less than about 22 Å, and the binding of a modulating member specific binding partner to said modulating member prevents, by steric inhibition, the binding of at least one of the members to a binding partner of that member.

22. The preparation of claim 21 wherein the modulating member is separated from the other two members by less than about 20 Å.

23. The preparation of claim 21 wherein the modulating member is selected from the group consisting of theophylline and theophylline-amine.

24. The preparation of claim 21 wherein at least one of the two members separated from each other by at least about 28 Å is selected from the group consisting of biotin and DNP.

25. A preparation comprising at least two trifunctional conjugate molecules, each trifunctional conjugate having a first member, a modulating member and a third member, each member being attached to an organic spacer moiety; wherein:
  the organic spacer moiety comprises ω-carbobenzoxylysine;
  (ii) the first member is biotin;
  (iii) the modulating member is theophylline; and
  (iv) the third member is dinitrophenol.

26. A trifunctional conjugate having a first member, a second member and a third member, each member being attached to an organic spacer moiety, wherein:
  (a) the first member is an azide residue capable of binding to at least one macromolecule;
  (b) the second member is a phenyl boronic acid residue capable of binding to at least one macromolecule;
  (c) the third member is selected from the group consisting of labels and solid supports; and
  (d) the spacer moiety is selected such that the binding of the azide residue to a macromolecule does not prevent the binding of the phenyl boronic acid residue to said macromolecule.

27. The trifunctional conjugate of claim 26 wherein the first member is a nitro-phenylazido residue.

28. The trifunctional conjugate of claim 27 wherein the third member is biotin.

29. The trifunctional conjugate of claim 26 wherein the third member is a label selected from the group consisting of biotin, radioactive compounds and enzymes.

30. The trifunctional conjugate of claim 26 wherein said organic spacer moiety is selected from the group consisting of cysteine, lysine, glutamic acid, pyroglutamic acid, S-acetylmecraptosuccinic anhydride, and ω-carbobenzoxylysine.

* * * * *